United States Patent [19]
Honda et al.

[11] Patent Number: 5,695,952
[45] Date of Patent: Dec. 9, 1997

[54] METHOD FOR PRODUCING [LEU$^{13}$] MOTILIN

[75] Inventors: Shinkichi Honda, Kanagawa; Tatsunari Nishi, Tokyo; Seiga Itoh, Kanagawa; Moriyuki Sato, Tokyo, all of Japan

[73] Assignee: Kyowa Hakko Kogyo Co., Ltd., Tokyo, Japan

[21] Appl. No.: 450,384

[22] Filed: May 25, 1995

Related U.S. Application Data

[62] Division of Ser. No. 387,566, Feb. 13, 1995, which is a continuation of Ser. No. 94,915, Jul. 22, 1993, Pat. No. 5,420,113, which is a continuation-in-part of Ser. No. 781,655, Oct. 25, 1991, abandoned, which is a continuation of Ser. No. 602,388, Oct. 24, 1990, abandoned, which is a continuation of Ser. No. 94,886, Sep. 10, 1987, abandoned.

[30] Foreign Application Priority Data

Dec. 9, 1986 [JP] Japan .......... SHO-61-215088

[51] Int. Cl.$^6$ .......... C12N 21/00
[52] U.S. Cl. .......... 435/68.1; 435/69.1; 435/69.7; 435/91.1; 435/252.2; 435/252.33; 435/320.1
[58] Field of Search .......... 435/68.1, 69.1, 435/69.7, 91.1, 252.2, 252.33, 320.1

[56] References Cited

U.S. PATENT DOCUMENTS

| | | | |
|---|---|---|---|
| 4,737,487 | 4/1988 | Watts | 530/328 |
| 4,769,326 | 9/1988 | Rutter | 435/172.3 |

FOREIGN PATENT DOCUMENTS

| | | |
|---|---|---|
| A- 0163406 | of 1985 | European Pat. Off. . |
| B- 2544348 | of 1977 | Germany . |
| 1507243 | 4/1978 | Germany . |
| A-54-9267 | 1/1979 | Japan . |
| 61-26559 | 6/1986 | Japan . |
| WO-A-8607383 | of 1986 | WIPO . |

OTHER PUBLICATIONS

Wuensch et al., Chem. Abstr. vol. 84, No. 150978y (1976).
Peeters, Chem Abstr. vol. 106, No. 19072g (1987).
Lehninger, Principles of Bi9ochemistry, Worth Publishers, pp. 95–117 (1982).
Mahler et al., Basic Biological Chemistry, Harper & Row, New York, pop 401–402 (1968).
Hall et al., Gastroenterology, vol. 87, pp. 76–85 (1984).
Peeters, Regulatory Peptides, vol. 23, pp. 171–182 (1988).
Wuensch et al., Chem. Abstr. vol. 87, No. 39848d (1977).
Koda et al., Chem. Abstr. vol. 109, No. 21513d (1988).
J.C. Brown et al, Can. J. Biochem., 51, pp. 33–537 (1973).
E. Wuensch et al, Z. Naturforsch., 28, pp. 235–240 (1973).
J.S. Brown et al Can. J. Biochem., 52, 7–8 (1974).
E. Wuensch et al, Hoppe–Seyler's Z. Physiol. Chem., 357, pp. 447–458.
E. Wuensch et al, ibid., 357, 459–465 (1976).
E. Wuensch et al, 357, 467–476 (1976).
E. Wuensch et al Scand. J. Gastroent., 11, Suppl. 39, pp. 19–24 (1976).
V. Strunz et al Scand. J. Gastroent., 11, 199–203 (1976).
J.C. Sarles, Horm. Metab. Res., 13, 340–342 (1981).
J.E.T. Fox et al, "Gastrointestinal Motility", pp. 59–65 (1980).
T.L. Peeters et al, Regulatory Peptides, 15, pp. 333–339 (1986).
T.L. Peeters et al Biomedical Research, 9(5), pp. 361–366 (1988).
Fluka's Catalogues Fluka Chemie Abs, Buchs, Switzerland pp. 164, 673, 807–808 (1989).
Y. Kai et al Chem. Pharm. Bull., 23(10), pp. 2346–2352 (1975).
M. Fujino et al Peptide Chemistry, 15, pp. 171 (1978).
S. Shinagawa et al Chem. Pharm. Bull., 26(3), pp. 880–884 (1978).
J.R. Reeve, Jr. et al, Journal of Chromatogrpahy 321, pp. 421–432.
M. Fujino et al Chem. Pharm. Bull, 26, pp. 101 (1978).
Chemical Pharm. Bulletin, vol. 26, No. 1, 1978, M. Fujino et al "Synthesis of Procine Motlin and its D–Phe–Analog by the Use of . . . ".
Patent Abstracts of Japan, vol. 1, No. 75, (C–020), 19 Jul. 1977.

Primary Examiner—Frank C. Eisenschenk
Attorney, Agent, or Firm—Nixon & Vanderhye P.C.

[57] ABSTRACT

A novel motilin analog peptide containing leucine instead of the usual 13th amino acid methionine, as in the naturally occurring motilin, is produced by gene recombination techniques in which several or identical genes, each coding for the novel peptide, are joined in series into a vector. The resultant recombinant DNA is introduced into *Escherichia coli* and the resultant transformant is cultivated. The resulting polymeric peptide can be cleaved to give the desired peptide.

2 Claims, 15 Drawing Sheets

METHOD FOR PRODUCING [LEU¹³] MOTILIN

This is a division of application Ser. No. 08/387,566, filed Feb. 13, 1995 which is a continuation of Ser. No. 08/094,915, filed Jul. 22, 1993, now U.S. Pat. No. 5,420,431 which is a continuation-in-part of Ser. No. 07/781,655 filed Oct. 25, 1991 abandoned which is a continuation of Ser. No. 07/602,388 filed Oct. 24, 1990 abandoned which is a continuation of Ser. No. 07/094,886 filed Sep. 10, 1987 abandoned.

FIELD OF THE INVENTION

This invention relates to a novel peptide which is a motilin analog containing leucine (Leu) in lieu of the 13th amino acid methionine (Met) of motilin, to DNAs coding for said peptide, to recombinant DNAs containing said DNAs, and to methods of producing these.

The novel peptide (hereinafter referred to as [Leu$^{13}$] motilin) according to the invention is comparable in activity to naturally occurring motilin, hence can be expected to be useful as a drug.

BACKGROUND OF THE INVENTION

Motilin is a physiologically active peptide occurring in the mammalian blood and is known to be capable of activating peristalsis of the intestine (W. Y. Chey and K. Y. Lee, *Clinics in Gastroenterology*, 3, 645 (1980)). Laparotomized patients show decreased motilin concentrations in the blood, and is known that the return of postoperative blood motilin concentrations to a normal level is correlated with the restoration of peristaltic movement of the intenstine in such patients and that post-operative administration of motilin results in activated peristalsis of the intestine.

Natural motilin can be obtained by extraction from animal organs but in insufficient quantities. Therefore, motilin in current use is mostly a product of chemical peptide synthesis. However, this chemical product is necessarily expensive since motilin is a relatively long chain peptide composed of 22 amino acid residues. Accordingly, it is desired that a substance having motilin activity be supplied at low cost and in large quantities.

The 13th amino acid of motilin is Met, which is readily oxidizable. Oxidation of Met to the sulfoxide form results in decreased motilin activity (M. Fujino et al., *Chem. Pharm. Bull.*, 26, 101 (1978)).

SUMMARY OF THE INVENTION

AS a result of their investigations made in an attempt to find a method of preventing the loss of motilin activity, the present inventors found that a peptide resulting from replacement in motilin of the 13th amino acid Met with Leu, namely [Leu$^{13}$]motilin, is comparable in activity to motilin but does not suffer the loss of activity caused by oxidation.

Furthermore, as a result of their investigations made in an attempt to find a method of supplying [Leu$^{13}$]motilin at low cost and in large quantities, the inventors found that [Leu$^{13}$] motilin can be supplied utilizing gene recombination techniques.

It is said that large scale production of small-molecule peptides using genetic engineering techniques is generally difficult. This is supposedly because the small-molecule peptides produced in host cells, for example, microbial cells, are readily decomposed under the action of enzymes in those cells. For preventing such decomposition, a method has been reported which comprises producing the desired peptide in the form of a high-molecular-weight fused protein resulting from fusion of the desired peptide with another protein, then decomposing, either enzymatically or chemically, the fused protein to yield the desired peptide (T. Mikuni et al., *Seikagaku*, 57, 854 (1985) and T. Saito et al., *Biochem.*, 102, 111 (1987)).

Another method has been proposed which comprises joining the gene coding for the desired peptide in series, producing the polymeric peptide, then decomposing enzymatically or chemically the polymeric peptide to obtain the desired monomeric peptide.

It has been reported that human proinsulin can be present in *Escherichia coli* more stably in the polymeric form than in the monomeric one (S. -H. Shen, *Proc. Natl. Acad. Sci. USA*, 81, 4627 (1947)). However, in this prior art, an attempt of conversion of the polymeric peptide to the desired monomeric peptide were not made.

The above-described method was applied to the production of Substance P (T. Kempe et al., *Gene*, 39, 239 (1985)) and growth hormone releasing factor (T. Kempe et al., *Biotechnology*, 4, 565 (1986)). In these cases, the monomeric peptides which are obtained by decomposing the polymeric peptide produced are different in the structure from the desired naturally occurring peptide.

As a matter of course, however, the yield of the desired peptide obtainable by the above method is low since the fused protein so produced contains only a small percentage of the desired peptide.

The present inventors found that the novel peptide according to the invention can be produced in a polymeric from by inserting a plurality of different or identical genes each coding for said peptide joined in series into a vector, introducing the resultant recombinant DNA into *Eschericia coli* and cultivating the resultant transformant, then cleaving the polymeric peptide to give the desired peptide.

BRIEF DESCRIPTION OF THE DRAWINGS

In the accompanying drawings.

GTCAGCGGATCCTGTAAGA-
GCT 3' (Formula 5)  SEQ ID NO:4

5' CTTACAGGATCCGCTGACCTTTGTTA-
CGTTCTTTCTCTTGCAGACG-
TTGC 3' (Formula 6)  SEQ ID NO:5

In the above formulae and hereinafter, A, T, G and C represent the bases adenine, thymine, guanine and cytosine in the nucleotides, respectively.

These DNAs are synthesized in the manner of solid phase synthesis by the phosphoramidide method using an automated DNA synthesizer.

The double-stranded DNA fragment formed from the DNA of Formula 3 (hereinafter, DNA 3) and the DNA of Formula 4 (hereinafter, DNA 4) and the one formed from the DNA of Formula 5 (hereinafter, DNA 5) and the DNA of Formula 6 (hereinafter, DNA 6) are joined together using ligase. Thus is constructed a double-stranded DNA of the formula given below (hereinafter referred to as "gene 2").

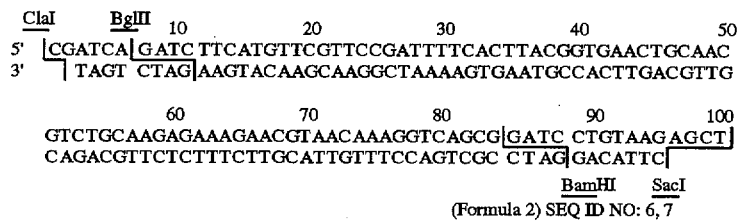

(Formula 2) SEQ ID NO: 6, 7

DETAILED DESCRIPTION OF THE INVENTION

The invention thus provides a novel peptide ([Leu$^{13}$]motilin) having the amino acid sequence defined by the following formula:

| 1 | 2 | 3 | 4 | 5 | 6 | 7 | 8 | 9 | 10 |
|---|---|---|---|---|---|---|---|---|---|
| Phe | Val | Pro | Ile | Phe | Thr | Tyr | Gly | Glu | Leu |

| 11 | 12 | 13 | 14 | 15 | 16 | 17 | 18 | 19 | 20 |
|---|---|---|---|---|---|---|---|---|---|
| Gln | Arg | Leu | Gln | Glu | Lys | Glu | Arg | Asn | Lys |

| 21 | 22 | | | | | | | | |
|---|---|---|---|---|---|---|---|---|---|
| Gly | Gln | | | | | | | | |

(Formula 1) SEQ ID NO: 1 wherein the symbols represent the respective amino acid residues as follows: Phe, phenylalanine; Val, valine; Pro, proline; Ile, isoleucine; Thr, threonine; Tyr, tyrosine; Gly, glycine; Glu, glutamic acid; Leu, leucine; Gln, glutamine; Arg, arginine; Lys, lysine; and Asn, asparagine (hereinafter the same designations shall apply throughout the specification and appended claims).

[Leu$^{13}$]motilin can be synthesized by the solid phase method of peptide synthesis (G. Barang et al., "The Peptide: Analysis, Synthesis, Biology" (edited by E. Gross and J. Meienhofen), vol. 2, p.1, Academic Press (1982)) using an automatic peptide synthesizer (e.g. Beckman model 990B).

Figure 1:
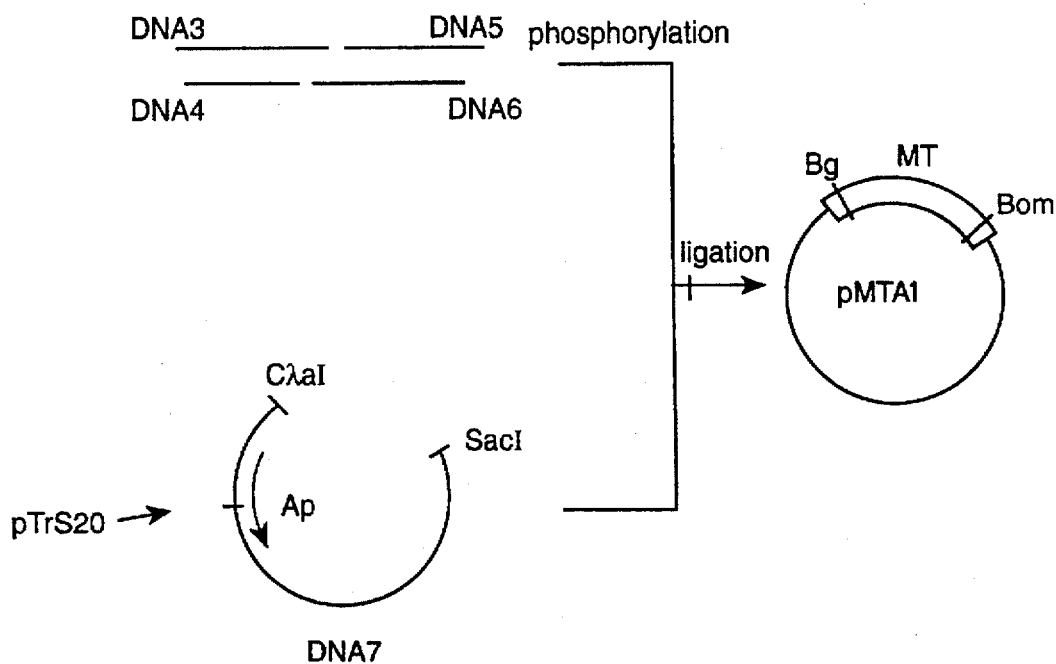
FIG. 1 shows a construction scheme for the plasmid pMTA1.

[Leu$^{13}$]motilin can also be produced by making the most use of genetic engineering techniques as follows:

Step 1 (cf. FIG. 1)

Firstly, DNAs defined by the formulae given below (Formulae 3–6) are chemically synthesized:

5' CGATCAGATCTTCATGTTCGTTCCGATTTT-
CACTTACGGTGAACTGCAAC 3' (Formula 3) SEQ ID NO:2

5' AGTTCACCGTAAGTGAAAATCGGAAC-
GAACATGAAGATCTGAT 3' (Formula 4) SEQ ID NO:3

5' GTCTGCAAGAGAAAGAACGTAACAAAGwherein the lead lines directed to the symbols ClaI, BglII, BamHI and SacI indicate the sites of cleavage by the respective restriction enzymes represented by said symbols.

This gene 2 has a base sequence coding for a peptide composed of 30 amino acids with aspartic acid (Asp)-glutamine (Gln)-isoleucine (Ile)-phenylalanine (Phe)-methionine (Met) being bound to the amino terminus of [Leu$^{13}$]motilin and arginine (Arg)-isoleucine (Ile)-leucine (Leu) being bound to the carboxyl terminus. The DNA segments coding for the amino acids bound to the amino terminus and carboxyl terminus of [Leu$^{13}$]motilin contain sites recognizable by the restriction enzymes BglII and BamHI and these sites are of use in constructing genes coding for [Leu$^{13}$]motilin polymers. Gene 2 has been designed such that two neighboring [Leu$^{13}$]motilin monomers in the polymers produced on the basis of these genes are connected to each other via a peptide (spacer peptide) composed of 4 amino acids, Arg-Ile-Phe-Met. This spacer peptide can be eliminated by treatment in sequence with cyanogen bromide, carboxypeptidase A and carboxypeptidase B to give monomeric [Leu$^{13}$]motilin. On both ends of gene 2, there are disposed sites recognizable by the restriction enzymes ClaI and SacI for introduction into vectors. The codons used in gene 2 are mostly those codons that are found with high frequency in the genes coding for proteins producible in large quantities in Escherichia coli (M. Goug et al., Nucleic Acids Res., 10, 7055 (1982)).

Gene 2 is synthesized by joining the double-stranded DNA fragment from DNA 3 and DNA 4 to the double-stranded DNA fragment from DNA 5 and DNA 6 using ligase. For efficient progress of this ligation reaction, gene 2 has been designed such that identical sequences longer than a certain length be not contained in the base sequence of gene 2.

Step 2 (cf. FIG. 1)

Figure 2:
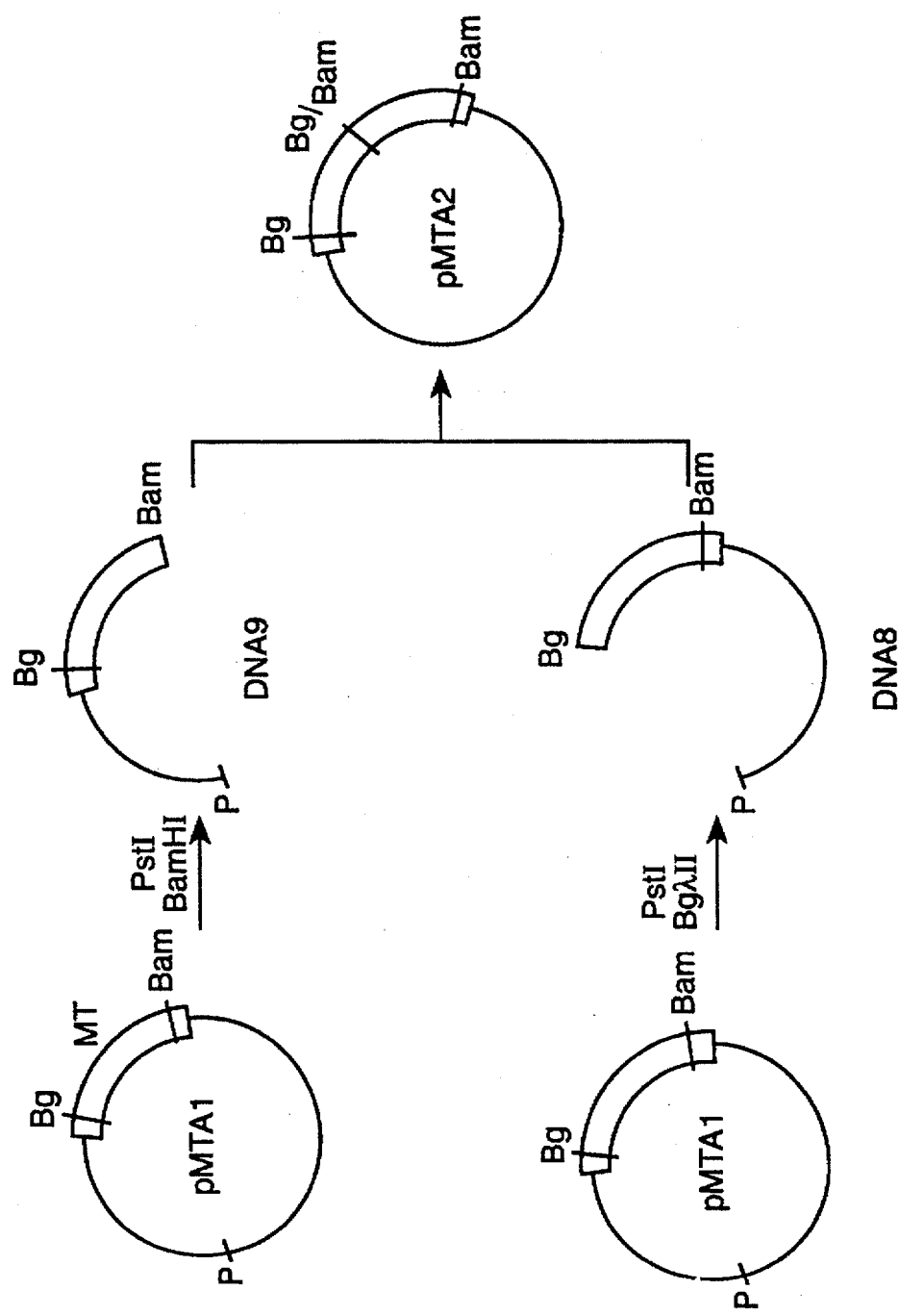
FIG. 2 shows a construction scheme for the plasmid pMTA2, wherein Bg, Bam and P indicate the sites of recognition by BglII, BamHI and PstI, respectively, and MT indicates a [Leu$^{13}$]motilin gene (hereinafter the same designations shall apply)

Construction of a plasmid containing gene 2:

The plasmid pTrS20 (prepared by the procedure of Reference Example 1) is cleaved with the restriction enzymes ClaI and SacI and a larger DNA fragment (hereinafter, DNA 7) is isolated. DNA 7 is joined to the gene obtained in step 1 using ligase, whereby the plasmid pMTA1 is constructed.
Step 3 (cf. FIG. 2)

Figure 3:
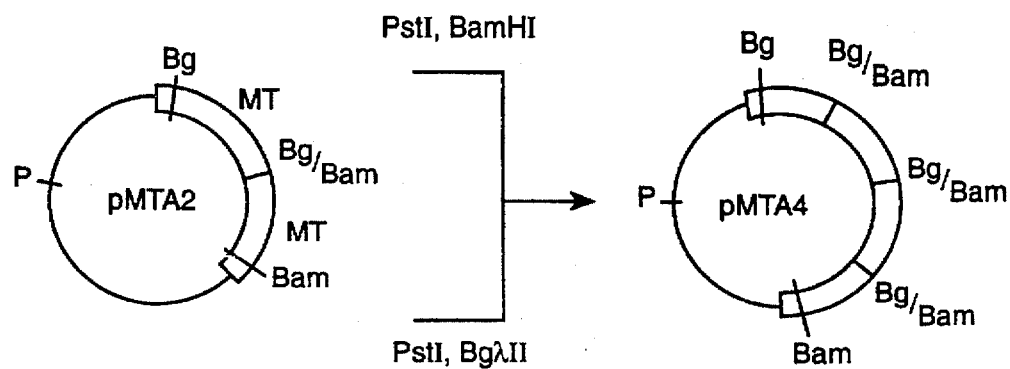
FIG. 3 shows a construction scheme for the plasmid pMTA4.

Construction of a plasmid containing two [Leu$^{13}$]motilin genes:

The plasmid pMTA1 is cleaved with the restriction enzymes PstI and BglII and a DNA fragment containing the [Leu$^{13}$]motilin gene (hereinafter, DNA 8) is isolated. Separately, pMTA1 is cleaved with PstI and BamHI and a DNA fragment containing the [Leu$^{13}$]motilin gene (hereinafter, DNA 9) is isolated. Ligation of DNA 8 with DNA 9 using ligase gives the plasmid pMTA2 containing two [Leu$^{13}$]-motilin genes. The cleavage ends resulting from treatment with the restriction enzymes BglII and BamHI are identical and therefore can be joined together. The ligation site (indicated by Bg/Bam in FIG. 2) is not cleaved with either of the restriction enzymes, however, since it now differs in base sequence from the recognition sites for both restriction enzymes.
Step 4 (cf. FIG. 3)

Construction of a plasmid containing four [Leu$^{13}$]motilin genes:

pMTA 2 is cleaved with PstI and BglII. Since, as mentioned above, the Bg/Bam site is not cleaved, there is obtained a DNA fragment containing two [Leu$^{13}$]motilin genes. Separately, pMTA2 is cleaved with PstI and BamHI to give a DNA fragment containing two [Leu$^{13}$]motilin genes in like manner. Joining both DNA fragments with ligase gives the plasmid pMTA4 containing four [Leu$^{13}$] motilin genes.

Figure 4:
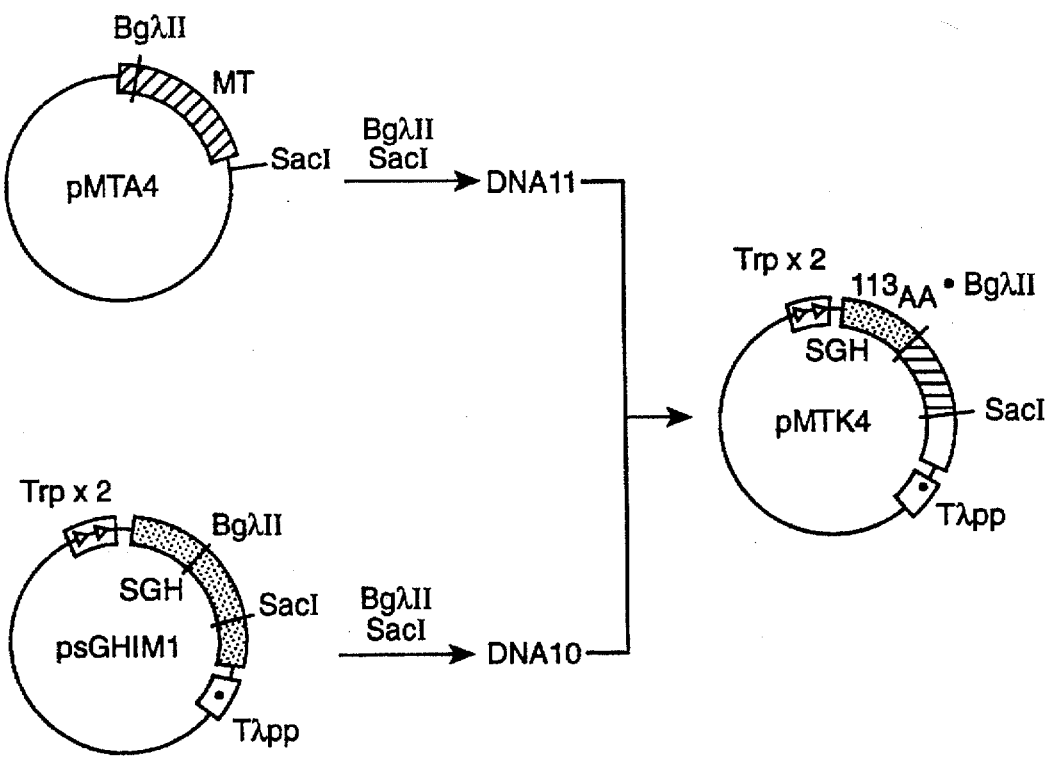
FIG. 4 shows a construction scheme for the plasmid pMTK4, wherein SGH indicates the salmon growth hormone gene (hereinafter the same designation shall apply)

The plasmids pMTA8, pMTA16 and pMTA32 which contain eight, sixteen and thirty-two [Leu$^{13}$]motilin genes, respectively, can be prepared in the same manner as in the construction of pMTA4 from pMTA2. Hereinafter, these are referred to generically as "pMTAs".
Step 5 (cf. FIG. 4)

Insertion of the [Leu$^{13}$]motilin gene into a vector for protein expression:

The plasmid psGHIM1 (produced by the procedure of Reference example 2) useful in the expressing of the salmon growth hormone (SGH) gene is cleaved with the restriction enzymes BglII and SacI and a larger DNA fragment (hereinafter, DNA 10) is isolated. Separately, the plasmid pMTA4 is cleaved with BglII and SacI and a DNA fragment containing four [Leu$^{13}$]motilin genes (hereinafter, DNA 11) is isolated. Joining DNA 10 to DNA 11 using ligase gives the expression plasmid pMTK4.

Figure 5:
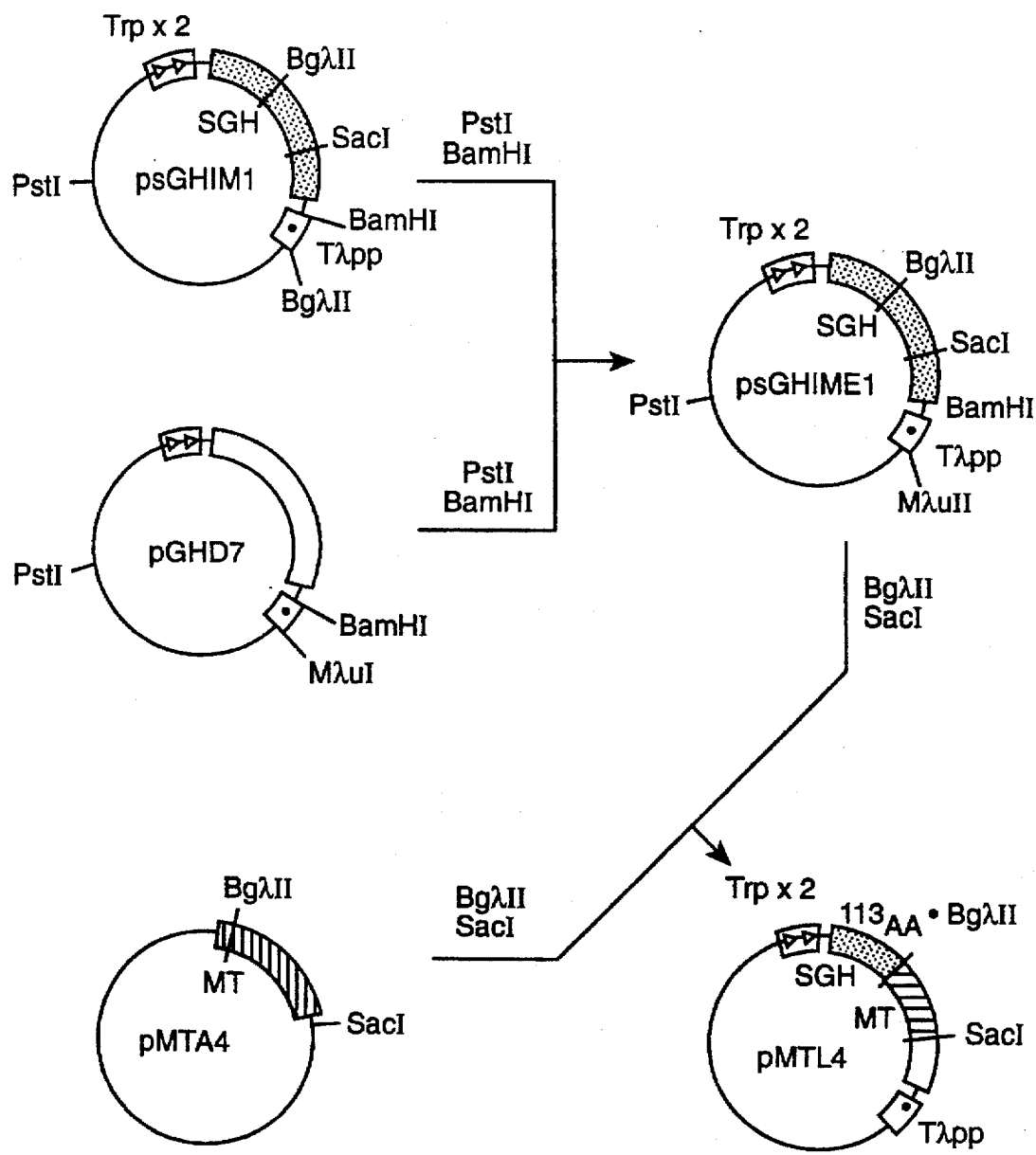
FIG. 5 shows a construction scheme for the plasmid pMTL4, wherein Tlpp indicates the lipoprotein terminator and Trp indicates the tryptophan promoter.

Using pMTA8 or pMTA 16 in lieu of pMTA4 and proceeding in the same manner as above, one may obtain the expression plasmid pMTK8 or pMTK16 containing eight or sixteen [Leu$^{13}$]motilin genes, respectively. Hereinafter, these are referred to generically as "pMTKs".
Step 6 (cf. FIG. 5)

Introduction of a terminator into the expression plasmid:

The plasmid psGHIM1 is cleaved with the restriction enzymes PstI and BamHI and a promoter-containing DNA fragment is recovered. Separately, the plasmid pGHD7 (Reference Example 4) is cleaved with PstI and BamHI to give a terminator-containing DNA fragment. By joining both DNA fragments together using ligase, there is constructed the plasmid psGHIME1 having no recognition site for the restriction enzyme BglII but having an MluI recognition site downstream from the terminator.

The larger DNA fragment obtained by cleavage of psGHIME1 with BglII and SacI is ligated with the [Leu$^{13}$] motilin gene-containing DNA fragment obtained by cleavage of pMTA4 with BglII and SacI in the presence of ligase to give the plasmid pMTL4, which contains four [Leu$^{13}$] motilin genes. Using pMTK8 or pMTK16 in lieu of pMTA4 and proceeding in the same manner as above, there is obtained the plasmid pMTL8 or pMTL16 containing eight or sixteen [Leu$^{13}$]motilin genes, respectively. Hereinafter, these are referred to generically as "pMTLs".

The plasmids pMTKs and pMTLs each contain a gene located downstream from the tryptophan promoter and coding for the 104 amino acids (from the amino terminus) of the salmon growth hormone. Downstream from this gene, a [Leu$^{13}$]motilin gene-containing gene is connected. Further, the terminator for the liporotein gene is introduced downstream from the last [Leu$^{13}$]motilin gene. The difference between the pMTK plasmids and pMTL plasmids lies in that pMTKs have a recognition site for the restriction enzyme BglII as situated downstream from the terminator while pMTLs do not have such a site.
Step 7

Figure 6:
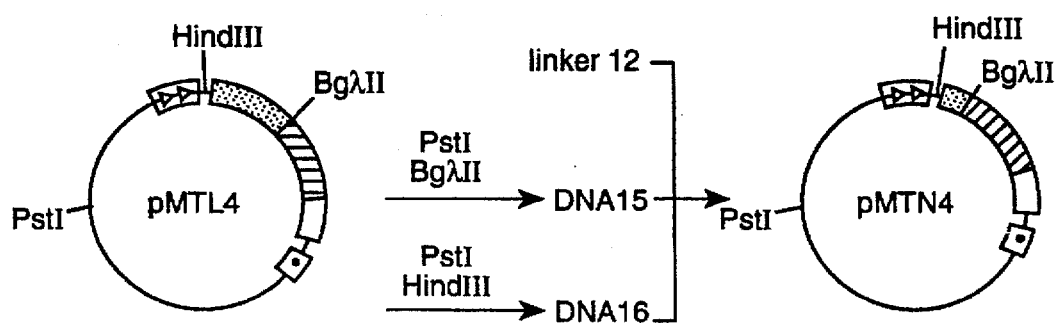
FIG. 6 shows a construction scheme for the plasmid pMTN4.

Expression of the [Leu$^{13}$]motilin gene:

The [Leu$^{13}$]motilin gene expression plasmids pMTKs and pMTLs are each introduced into *Escherichia coli*. The transformant produces a fused protein composed of [Leu$^{13}$] motilin tetramer, octamer or hexadecamer and the salmon growth hormone. The thus-produced fused proteins occur as granules in *Escherichia coli* cells. The production of the fused protein derived from [Leu$^{13}$]motilin tetramer is highest and accounts for about 10% of the total amount of the cell proteins. The content of [Leu$^{13}$]motilin in the granules is 42% for pMTL4, 56% for pMTL8 and 68% for pMTL16.
Step 8 (cf. FIG. 6)

Improvement in the yield of Leu$^{13}$ motilin-(1):

The above method using the pMTK and pMTL plasmids gives [Leu$^{13}$]motilin in the form of the desired peptide fused to the protein portion of the salmon growth hormone which is composed of 104 amino acids. It is desirable that this salmon growth hormone portion be as small as possible. A plasmid in which the salmon growth hormone portion is shorter can be constructed in the manner mentioned below for the enhanced production of [Leu$^{13}$]motilin.

A deoxyoligonucleotide of the formula given below (Formula 13) (hereinafter, DNA 13) and a deoxyoligonucleotide of the formula given below (Formula 14) (hereinafter, DNA 14) are chemically synthesized. The synthesis is performed in the manner of solid synthesis by the phosphoramidite method using an automatic DNA synthesizer.

5' AGCTTATGATAGAAAACCAACGGCTCTTCCA 3' (Formula 13)    SEQ ID NO:8

5' GATCTGGAAGAGCCGTTGGTTTTCTATCATA 3' (Formula 14)    SEQ ID NO:9

Both the DNAs are mixed together and a linker of the formula given below (Formula 12).

5' AGCTTATGATAGAAAACCAACGGCTCTTCCA SEQ ID NO:8

3' ATACTATCTTTTGGTTGCCGAGAAGGTCTAG (Formula 12)

Linker 12 contains a gene coding for the amino terminal amino acid to the 8th amino acid of the salmon growth hormone and, on both sides of that gene, the same cohesive ends as produced by the restriction enzymes HindIII and BglII.

The plasmid pMTL4, which contains four [Leu$^{13}$]motilin genes, is cleaved with the restriction enzymes PstI and BglII, and a [Leu$^{13}$]motilin gene-containing DNA fragment (hereinafter, DNA 15) is isolated. Separately, pMTL4 is cleaved with the restriction enzymes PstI and HindIII, and a promoter-containing DNA fragment (hereinafter, DNA 16) is isolated. DNA 15, DNA 16 and linker 12 are joined together using ligase. Thus is constructed the plasmid pMTN4.

The use of pMTL8 in lieu of pMTL4 together with the above procedure leads to the construction of pMTN8. The plasmids pMTN4 and pMTN8 each contain a gene coding for a protein composed of the corresponding [Leu$^{13}$]motilin polymer and 12 amino acids, Met-Ile-Gln-Asn-Gln-Arg-Leu-Phe-Gln-Ile-Phe-Met, bound to the amino terminus of that polymer; pMTN4 has four [Leu$^{13}$]motilin genes and pMTN8 has eight [Leu$^{13}$]motilin genes. The plasmids pMTN4 and pMTN8 are each introduced into *Escherichia coli*. The resultant transformants produce the desired proteins in almost the same amounts as in the cases of the transformants carrying the pMTK or pMTL plasmids. Each of the proteins occur as granules in *Escherichia coli* cells. The [Leu$^{13}$]motilin content in the granules is 77–80% and is much higher than that in the case of the pMTK- or pMTL-carrying transformants.

Figure 7:
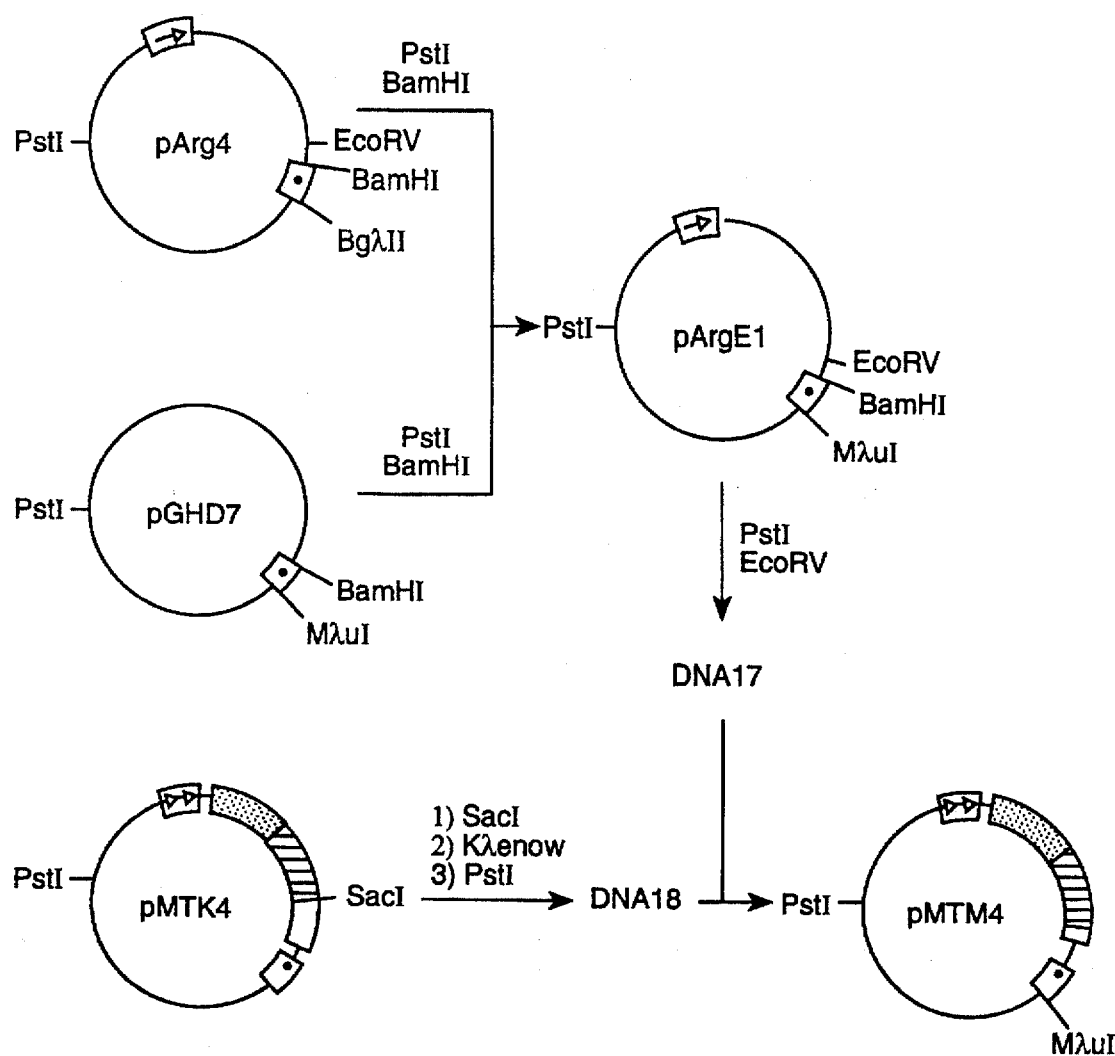
FIG. 7 shows a construction scheme for the plasmid pMTM4.

Step 8 (cf. FIG. 7)

Improvement in the yield of [Leu$^{13}$]motilin-(2):

While [Leu$^{13}$]motilin can be produced in large quantities by introducing the pMTK, pMTL, and pMTN plasmids into *Escherichia coli*, [Leu$^{13}$]motilin can be produced in higher yields by eliminating a part of the plasmid DNA, as shown below.

The pMTL plasmids have a terminator downstream from the [Leu$^{13}$]motilin genes. A plasmid lacking in the nontranslational (untranslated) region DNA between this terminator and the last [Leu$^{13}$]motilin gene is constructed.

Thus, the plasmid pArg4 (Reference Example 5) is cleaved with the restriction enzymes PstI and BamHI and a promoter-containing DNA fragment is recovered. Separately, pGHD7 is cleaved with PstI and BamHI and a terminator-containing DNA fragment is isolated. Both the DNA fragments are joined together using ligase to thereby construct the plasmid pArgE1 which has no BglII recognition site downstream from the terminator.

pArgE1 is cleaved with PstI and EcoRV and a terminator-containing DNA fragment (hereinafter, DNA 17) is isolated.

The plasmid pMTK4 is cleaved with the restriction enzyme SacI, and the single-stranded regions corresponding to the cleavage site are rendered blunt-ended by means of hydrolysis with DNA polymerase I, Klenow fragment. The DNA fragment is further cleaved with PstI and a [Leu$^{13}$]motilin gene-containing DNA fragment (hereinafter, DNA 18) is isolated. Joining DNA 17 to DNA 18 using ligase gives the plasmid pMTM4.

Using pMTL4 instead of the plasmid pMTK4 and proceeding in the same manner as above, pMTM4 is obtained.

Using mMTL8 instead of pMTK4 and proceeding in the same manner as above, the plasmid pMTM8, which contains eight [Leu$^{13}$]motilin genes is obtained.

pMTM8 can be constructed from pMTM4 in the same manner as in the construction of pMTA8 from-pMTA4. Thus, pMTM4 is cleaved with the restriction enzymes PstI and BglII and a [Leu$^{13}$]motilin gene-containing DNA fragment is isolated. This DNA fragment is joined, in the presence of ligase, to the [Leu$^{13}$]motilin gene-containing DNA fragment obtained by cleavage of pMTM4 with PstI and BamHI, to give pMTM8.

Furthermore, using pARG4 in lieu of the plasmid pArgE1 and proceeding in the same manner as in the construction of pMTM4 or pMTM8, the plasmids pMTm4 and pMTm8 are constructed. The difference between pMTMs and pMTms lies in that pMTms have a recognition site for the restriction enzyme BglII while pMTMs have no such site.

Step 9

Expression of the [Leu$^{13}$]motilin gene using pMTMs:

The pMTM and pMTm plasmids have a structure such that about 160 base pairs (hereinafter, bp) of the nontranslational region gene upstream from the terminator have been eliminated from pMTKs and pMTLs.

When pMTM4 is introduced into *Escherichia coli* HB101, the [Leu$^{13}$]motilin polymer protein content accounts for 17% of the total protein content.

Figure 8:
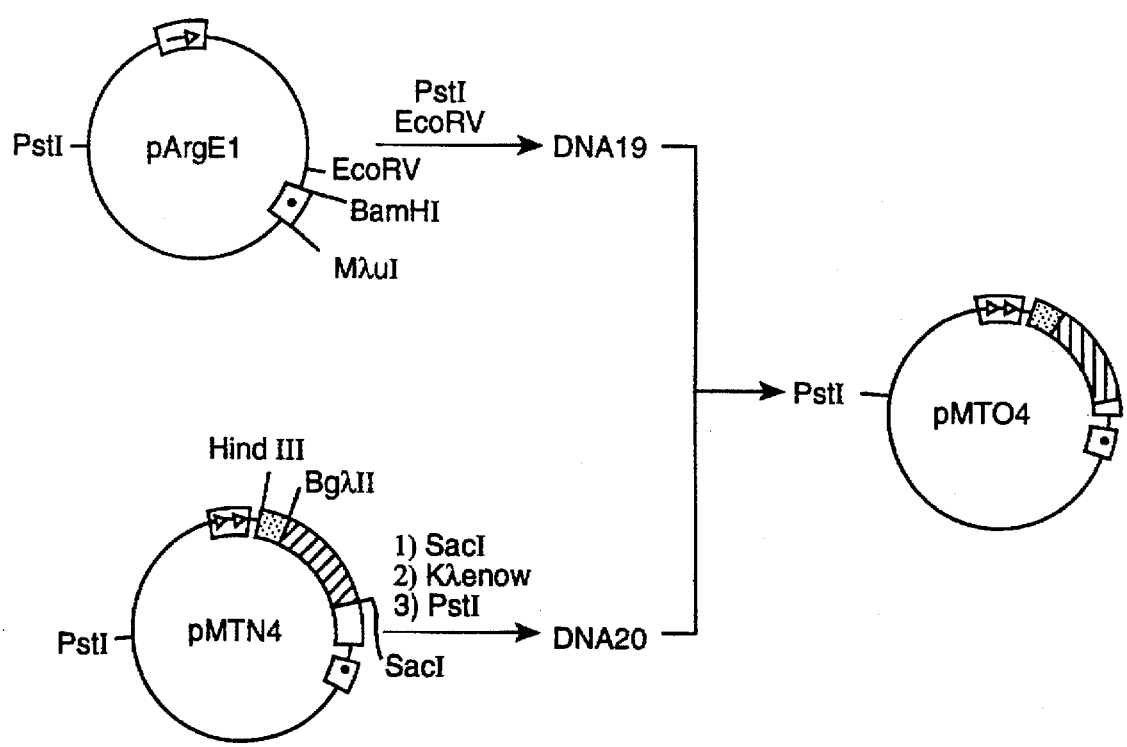
FIG. 8 shows a construction scheme for the plasmid pMTO4.

Step 10 (cf. FIG. 8)

Improvement in the yield of [Leu$^{13}$]motilin-(3):

The pMTN plasmids have a terminator downstream from the [Leu$^{13}$]motilin gene region. Plasmids, in which the nontranslational region gene between the terminator and the [Leu$^{13}$]motilin gene region has been eliminated, are constructed as follows:

The plasmid pArgE1 is cleaved with PstI and EcoRV and a terminator-containing DNA fragment (hereinafter, DNA 19) is isolated. The plasmid pMTN4 is cleaved with the restriction enzyme SacI, and the signle-stranded regions corresponding to the cleavage site are converted to blund ends by hydrolysis using DNA polymerase I, Klenow fragment. After further cleavage with the restriction enzyme PstI, a [Leu$^{13}$]motilin gene-containing DNA fragment (hereinafter, DNA 20) is isolated. Ligation of both DNA fragments using ligase gives the plasmid pMTO4.

pMTO8 is constructed using pMTN8 in lieu of pMTN4 and following the above procedure. Like pMTM8, pMTO8 can be prepared also by the method used in constructing pMTA8 from pMTA4.

A series of pMTo plasmids are constructed in the same manner as above using pArg4 in lieu of pArgE1. The pMTO plasmids differ from the pMTo plasmids in that the latter have a recognition site for the restriction enzyme BglII downstream from the terminator while the former have no such site.

The pMTO and pMTo plasmids have a structure such that about 160 bp of the nontranslational region gene upstream from the terminator have been eliminated from pMTNs. pMTO4 is introduced into *Escherichia coli* to cause protein expression. The transformant produces the protein equally in large amounts as is the case with pMTN4. The protein occurs as granules in the transformant strain, and the [Leu$^{13}$] motilin content in the granules is 77%.

Step 11

Figure 9:
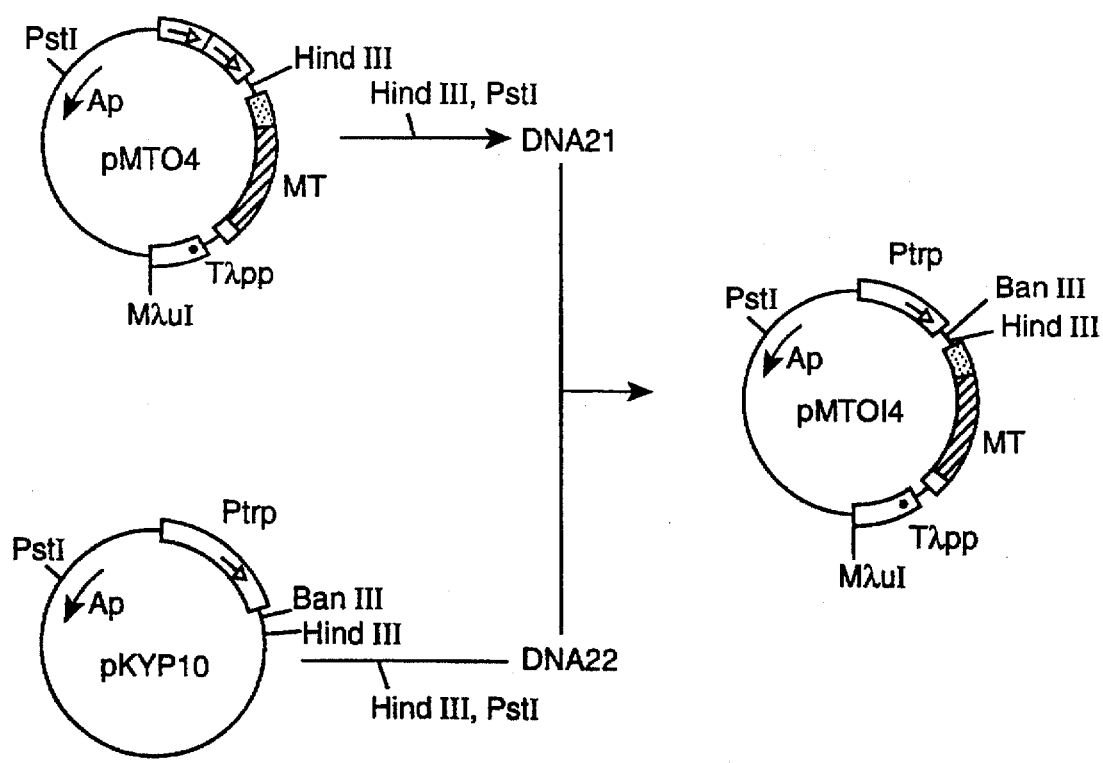
FIG. 9 shows a construction scheme for the plasmid pMTOI4.

Promoter modification:

The plasmid pMTO4 contains two tryptophan promoters coupled in series (Ptrp×2) and the distance between the Shine-Dalgarno (SD) sequence and the initiation codon (ATG) (SD-ATG) corresponds to 10 bases. The plasmid pMTO4 is cleaved with the restriction enzymes HindIII and PstI and a [Leu$^{13}$]motilin gene-containing DNA fragment (hereinafter, DNA 2i) is isolated. Separately, the plasmid pKYP10 (European Patent Publication No. 83069A) is cleaved with the restriction enzymes HindIII and PstI and a promoter-containing DNA fragment (hereinafter, DNA 22) is isolated. Ligation of DNA 21 with DNA 22 using ligase gives the plasmid pMTOI4 (cf. FIG. 9). The plasmid pMTOI4 contains one tryptophan promoter (Ptrp) and the SD-ATG distance therein corresponds to 14 bases.

Figure 10:
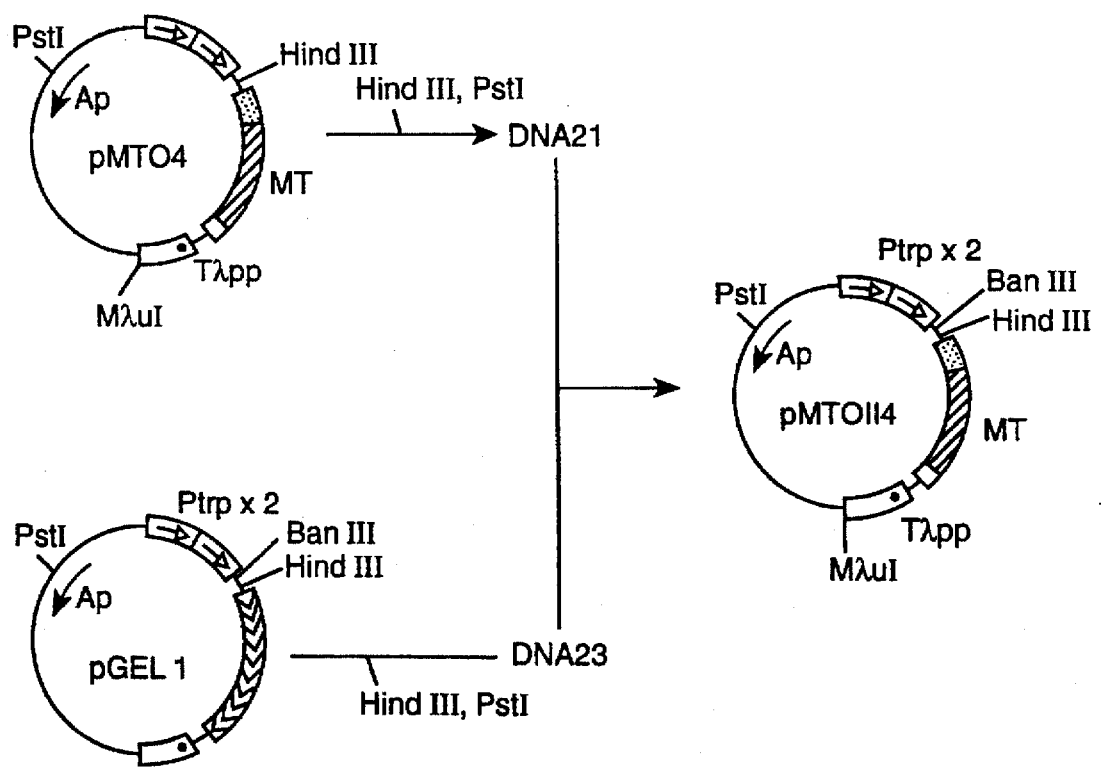
FIG. 10 shows a construction scheme for the plasmid pMTOII4.

The plasmid pGEL1 (European Patent Publication No. 166444A; FERM BP-612), which is used in lieu of the plasmid pKYP10, is cleaved with the restriction enzymes HindIII and PstI and a promoter-containing DNA fragment (hereinafter, DNA 23) is isolated. DNA 21 (obtained from the plasmid pMTO4) and DNA 23 are joined together using ligase, whereby the plasmid pMTOII4 is obtained (cf. FIG. 10). The plasmid pMTOII4 contains two promoters (Ptrp×2) and the SD-ATG distance therein amounts to 14 bases.

Figure 11:
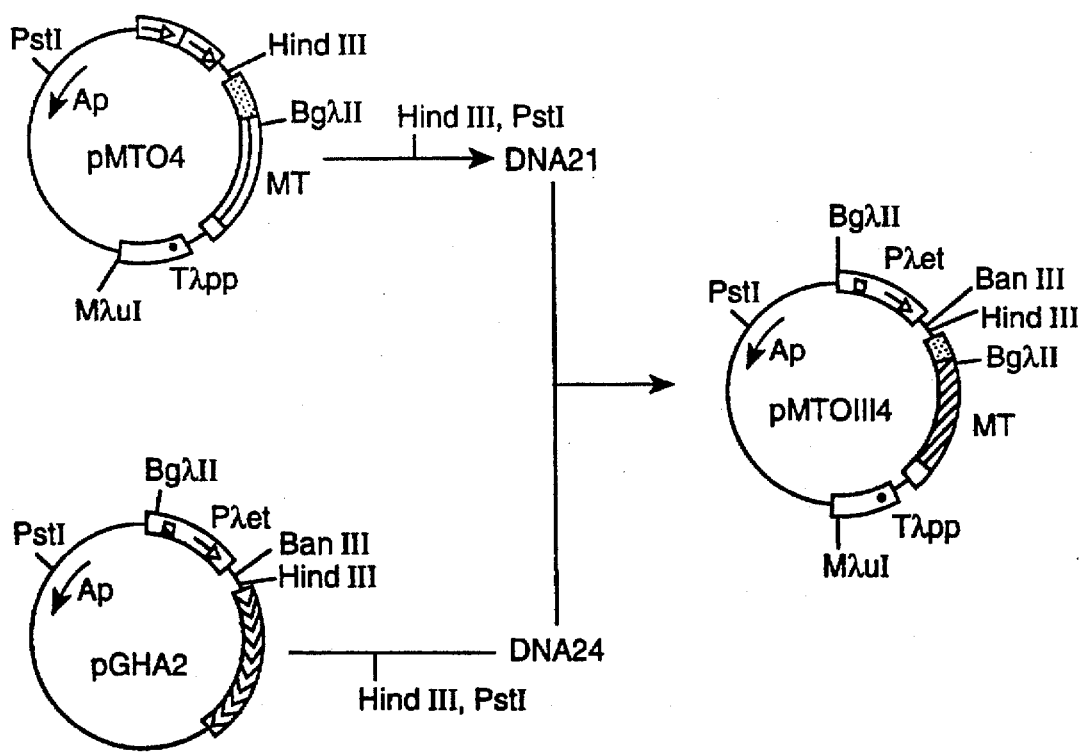
FIG. 11 shows a construction scheme for the plasmid pMTOIII4.

The plasmid pGHA2 (European Patent Publication No. 152613A; IGHA2; FERM BP-400), which is used in lieu of the plasmid pGEL, is cleaved with the restriction enzymes HindIII and PstI and a promoter-containing DNA fragment (hereinafter, DNA 24) is isolated. DNA 21 (obtained from the plasmid pMTO4) and DNA 24 are joined together using ligase to give the plasmid pMTOIII4 (cf. FIG. 11). The plasmid pMTOIII4 contains a let promoter (Plet) and the SD-ATG distance therein is 14 bases long.

Each [Leu$^{13}$]motilin polymer produced abundantly by virtue of the above genetic engineering techniques is accumulated, in the form of granules, in bacterial cells. The cells are disrupted and then subjected to centrifugation, whereby the granules are readily separated from the membrane components and soluble fractions. The [Leu$^{13}$]motilin polymer is thus obtained in good yields and in high purity. When this granular [Leu$^{13}$]motilin polymer is treated with cyanogen bromide for degradation, cleavage takes place at the site of the methionine in the spacer peptide, giving a peptide (peptide 25) composed of 26 amino acids, namely monomeric [Leu$^{13}$]motilin and Arg-Ile-Phe-Hse (methionine having been converted to homoserine (Hse) as a result of degradation) bound to the carboxyl side of said [Leu$^{13}$]motilin. Digestion of this peptide 25 with carboxypeptidase A results in hydrolytic elimination from the carboxyl side of Hse, Phe and Ile in that order. Thus is obtained a peptide (peptide 26) composed of [Leu$^{13}$]motilin and Arg bound to the carboxyl terminus thereof as a single product.

The subsequent digestion of peptide 26 with carboxypeptidase B eliminates Arg to give [Leu$^{13}$]motilin (Formula 1) as a single product in high yields.

Phe Val Pro Ile Phe Thr Tyr Gly Glu Leu Gln Arg Leu-Gln Glu Lys Glu Arg Asn Lys Gly Gln Arg Ile Phe Hse
(Peptide 25) SEQ ID NO: 10

Phe Val Pro Ile Phe Thr Tyr Gly Glu Leu Gln Arg Leu-Gln Glu Lys Glu Arg Asn Lys Gly Gln Arg
(Peptide 26) SEQ ID NO: 11

Phe Val Pro Ile Phe Thr Tyr Gly Glu Leu Gln Arg Leu-Gln Glu Lys Glu Arg Asn Lys Gly Gln
(Formula 1) (SEQ ID NO: 1)

As mentioned above, the production method according to the invention gives [Leu$^{13}$]motilin in very high yields by virtue of the genetic engineering techniques. The production method according to the invention consists in construction of a gene coding for a peptide polymer composed of a plurality of molecules of the desired peptide connected in series with a spacer peptide, which is eliminable chemically and enzymatically, inserted between every two molecules of the desired peptide; insertion of the gene into a plasmid having an effective promoter and a terminator; introduction of the resultant plasmid into a microorganism to thereby cause production of the peptide polymer in significant quantities; conversion of the thus-obtained peptide polymer to the desired monomeric peptide in high yields by chemical and enzymatic treatment; and recovering the desired peptide.

While the use of cyanogen bromide, carboxy peptidase A and carboxypeptidase B for spacer peptide elimination has been mentioned in this disclosure, any other elimination method can be employed provided that method used will not cause decomposition of the desired peptide. The use of formic acid, for instance, for chemical degradation, results in cleavage of the Asp-Pro bond, whereas hydroxylamine cleaves the Asn-X (X being Gly, Leu or Ala) bond. For enzymatic degradation, the use of enterokinase for cleaving the $(Asp)_n$-Lys (n=2 to 4) bond, the use of collagenase for cleaving Pro-X-Gly-Pro (X being any amino acid residue) and the use of kallikrein for cleaving the Phe-Arg bond may be mentioned, among others.

The spacer peptide to be employed in practicing the invention may have any structure that can be cleaved by a cleavage method which will not cause cleavage of the desired peptide and which is selected from among the cleavage methods as mentioned above, provided that the resultant spacer peptide fragment or fragments can be eliminated by a suitable method or methods. In processes for producing peptide monomers which involve production of polymers containing peptide monomers connected in series and cleavage of said polymers, the use of a spacer peptide is generally essential. The use of a spacer peptide is unnecessary only when a selective method is available for cleaving the bond between the amino terminus and carboxyl terminus of the peptide to be produced. For instance, in cases where the amino terminus is Pro and the carboxyl terminus is Asp, the peptide polymers in which monomer units are connected via the bond Asp-Pro can be converted to the monomeric form by treatment with formic acid. However, peptides having such structure are very scarce. Accordingly, spacer peptides are generally essential and they must be designed so that they can be cleaved and eliminated readily and in high yields.

The spacer peptide specifically disclosed herein has wide application as it can be used in producing all peptides that are free of methionine. Thus, when the carboxyl-terminal amino acid of the desired peptide is other than a basic amino acid, the spacer peptide according to the invention can be used and can be cleaved and eliminated as well by the method specifically disclosed herein. When the carboxyl-terminal amino acid of the desired peptide is the basic amino acid Lys or Arg, the basic amino acid Arg in the spacer peptide according to the invention is unnecessary and the reaction for spacer peptide elimination following cleavage with cyanogen bromide needs only carboxypeptidase A; carboxypeptidase B is unnecessary.

The gene coding for the spacer peptide according to the invention has recognition sites for the restriction enzymes BglII and BamHI and the utility of the method comprising combining, by means of said gene, a number of genes treated with enzymes producing the same cleavage termini has been demonstrated above. In combining a number of genes in series, a number of enzymes can be used in addition to the combination of BglII and BamHI which combination is preferably used in accordance with the invention. The only requirement is that the restriction enzymes used give cleavage sites to the base sequence coding for a spacer peptide which meets the above-mentioned conditions relative to cleavage and elimination.

While the gene production method has been described herein relative to genes containing $2^n$ (n=1 to 5) [Leu$^{13}$] motilin genes, namely 1, 2, 4, 8, 16 and 32 [Leu$^{13}$]motilin genes, joined together in series, respectively, it is evident that any optional number of genes coding for the peptide according to the invention can be connected with one another in series with ease by the relevant method disclosed herein. Although mention has been made herein of the production of [Leu¹³]motilin polymers in the form of fused proteins resulting from the connection of the genes coding for the polymers to a part of the gene for the amino terminal side of the salmon growth hormone or IFN-γ at a site downstream thereof, it will be understood that that part of salmon growth hormone or IFN-γ gene is not an essential element in producing the desired [Leu¹³]motilin polymers.

However, the base sequence in the vicinity of the initiation codon ATG of a gene has a great influence on the protein yield. The use of genes that have the base sequence around the initiation codon ATG of the salmon growth hormone gene, which is known to give high productivity, can result in the high-level expression of the [Leu¹³]motilin polymer genes. This method also allows high-level expression of genes for peptide polymers other than [Leu¹³]motilin polymers as well and accordingly has considerable general applicability beyond the specifics of making the [Leu¹³] motilin, as will be apparent.

The reaction conditions to be employed in the above recombinant DNA techniques are consistent with the usual techniques and are generally as follows:

The reaction for DNA digestion with a restriction enzyme or enzymes is carried out generally in a reaction mixture composed of 0.1–20 μg of DNA and a medium containing 2–200 mM (preferably 10–40 mM) Tris-HCl (pH 6.0–9.5, preferably pH 7.0–8.0), 0–200 mM NaCl or KCl, 2–30 mM (preferably 5–10 mM) MgCl$_2$ and 0–20 mM mercaptoethanol, with 0.1–100 units (preferably 1–3 units per microgram of DNA) of a restriction enzyme or enzymes added, at 20°–70° C. (the optimal temperature may vary depending on the restriction enzyme or enzymes used) for 15 minutes to 24 hours.

The DNA fragment formed upon restriction enzyme digestion is purified by the LGT method or by polyacrylamide gel electrophoresis, for instance.

The reaction for ligating DNA fragments is carried out in a reaction medium containing 2–200 mM (preferably 10–40 mM) Tris-HCl (pH 6.1–9.5, preferably pH 7.0–8.0), 2–20 mM (preferably 5–10 mM) MgCl$_2$, 0.1–10 mM (preferably 0.5–2.0 mM) ATP and 1–50 mM (preferably 5–10 mM) dithiothreitol, using 0.3–10 units of T4 DNA ligase, at 1°–37° C. (preferably 3°–20° C.) for 15 minutes to 72 hours (preferably 2–20 hours).

The recombinant plasmid DNA formed by the ligation reaction is introduced into *Escherichia coli*, as necessary by using the transformation method of Cohen et al. (S. N. Cohen et al., *Proc. Natl. Acad. Sci. USA*, 69, 2110 (1972)).

The DNA isolation from the *Escherichia coli* strain harboring the recombinant plasmid DNA is carried out by the cesium chloride-ethidium bromide density gradient ultracentrifugation method (D. B. Clewell et al., *Proc. Natl. Acad. Sci. USA*, 62, 1159 (1969)) or by the method of Birnboim et al. (H. C. Birnboim et al., *Nucleic Acids Res.*, 7, 1513 (1979)), for instance.

The plasmid DNA is digested with an appropriate restriction enzyme or enzymes and examined for the cleavage site or sites by agarose gel electrophoresis or polyacrylamide gel electrophoresis. If necessary, the base sequence of the DNA is further determined by the Maxam-Gilbert method (*Proc. Natl. Acad. Sci., USA*, 74, 560 (1977)) or by the Sanger's method which uses M13 phage (Sanger et al., *Proc. Natl. Acad. Sci., USA*, 74, 5463 (1977); Amersham's M13 Cloning and Sequencing Handbook).

The peptide according to the invention can be produced in the following manner:

*Escherichia coli* K-12 C600 or HB101, for instance, is transformed with the plasmid and plasmid-carrying *Escherichia coli* transformants are selected from among ampicillin-resistant colonies. By cultivating the plasmid-carrying *Escherichia coli* strains in a medium, peptide can be produced in the culture.

Any medium, either synthetic or natural, may be used as the growth medium, provided that it is suited for the growth of *Escherichia coli* and for the production of the peptide.

Usable as the carbon sources are glucose, fructose, lactose, glycerol, mannitol and sorbitol, among others. Usable as the nitrogen sources are, for example, NH$_4$Cl, (NH$_4$)$_2$SO$_4$, casamino acids, yeast extract, polypeptone, meat extract, Bactotryptone and corn steep liquor. K$_2$HPO$_4$, KH$_2$PO$_4$, NaCl, MgSO$_4$, vitamin B$_1$, MgCl$_2$, and so forth can be used as other nutrient sources.

The cultivation is carried out with aeration and stirring at a pH of 5.5 to 8.5 and at a temperature of 18°–40° C.

After 5–90 hours of cultivation, the peptide accumulated in cultured cells is recovered by harvesting cells from the culture, treating the same with lysozyme, disrupting the same by repeated freezing-thawing cycles, and extracting the peptide from the supernatant obtained by centrifugation by a conventional method of peptide extraction.

The peptide can be detected by directly dissolving the cultured cells in Laemmli's sample buffer (Laemmli, *Nature*, 227, 680 (1970)) with heating, and applying to SDS-polyacrylamide gel electrophoresis (Laemmli's method; vide supra), followed by straining with the dye Coomassie Brilliant Blue (Bio-Rad).

The following examples are further illustrative of the present invention.

EXAMPLE 1

Production of DNAs 3–6, 13 and 14:

DNAs 3–6, 13 and 14 were synthesized by phosphoramidide method in the manner of solid phase synthesis L. Beaucage et al., *Tetrahedron Letters*, 22, 1859 (1981); L. J. McBrie et al., ibid., 24, 245 (1983)) using an Applied Biosystems model 380A automatic DNA synthesizer, as follows:

Silica gel was used as the solid-phase carrier. (1) A nucleotide was condensed with the 5' hydroxyl group of a nucleotide bound to the solid-phase carrier via the 3'-hydroxyl group thereof by the phosphoramidide method, (2) the phosphite bond in the condensed nucleotide was oxidized in a phosphate bond with iodine, and (3) the protective group on the 5' hydroxyl group of the condensed nucleotide was removed with trifluoroacetic acid. Then, step (1) was repeated for the condensation of the next nucleotide. In this way, steps (1)–(3) were repeated, and a DNA was synthesized on the carrier. After completion of the synthesis, the carrier with the DNA bound thereto was allowed to stand in a thiophenol solution for 1 hour at room temperature to thereby cause elimination of the protective group on the phosphoric acid moiety and then allowed to stand in concentrated aqueous ammonia for 1 hour at room temperature, whereby the DNA was released from the carrier. The DNA-containing concentrated aqueous ammonia was heated at 60° C. in a sealed vessel for 12 hours to eliminate the protective groups on the bases.

In the case of DNA 3, for instance, the synthesis was carried out using 1 μM of the starting nucleotide bound to the carrier. After completion of the last condensation reaction in an overall yield of 81% and the subsequent deprotection and release from the solid phase, there was obtained DNA 3 as a crude product in a yield of 242 O.D. units (measured at 260 nm). For purification, 22 O.D. units of this crude product was electrophoresed on a 10% polyacrylamide gel (2 mm thick, 13 cm×13 cm) using tris-borate buffer (pH 8) containing 7M urea. That portion of the gel which contained DNA 3 was collected and extracted with 1 ml of 0.2M triethylamine carbonate buffer (pH 8) (hereinafter, TEAB) for 18 hours. The extract was applied to a SEPHADEX DE52® (Pharmacia Fine Chemicals) absorption column (6 mm in diameter, 5 mm in length) for causing DNA 3 to be adsorbed thereon. Elution with 2 ml of 2M TEAB gave 3.9 O.D. units of pure DNA 3.

Other DNAs than DNA 3 were also synthesized in almost the same yields.

These DNAs were radiolabeled by phosphorylating them on the 5'-hydroxyl group thereof by the conventional method (A. M. Maxam et a., *Methods in Enzymology*, vol. 65, part I, p. 499, Academic Press (1980)) using phage T4 nucleotide kinase and [γ-$^{32}$P]ATP. The labeled DNAs were subjected to 20% polyacrylamide gel electrophoresis using tris-borate buffer containing 7M urea. In this way, the purity and chain length of each DNA was confirmed. Furthermore, the base sequence of each labeled DNA was determined by the Maxam-Gilbert method (vide supra) and it was confirmed that each DNA had the respective desired base sequence.

EXAMPLE 2

Construction of the plasmid pMTA1:

The plasmid pTrS20 (2 μg) was dissolved in 30 μl of a solution (10 mM Tris-HCl (pH 7.5), 7 mM MgCl$_2$, 6 mM 2-mercaptoethanol) containing 10 units of the restriction enzyme ClaI (Boehringer Mannheim) and 15 units of the restriction enzyme SacI (Takara Shuzo), and the digestion reaction was carried out at 37° C. for 2 hours. The reaction mixture was electrophoresed on an ethidium bromide-containing agarose gel. Under detection with ultraviolet rays at a wavelength of 302 nm, a gel piece containing DNA 7 of about 3.8 kb was excised. To the gel piece was added 0.5 ml of phenol, the mixture was frozen and thawed, the aqueous layer was washed with chloroform, and the DNA was recovered by precipitation with ethanol.

DNAs 3–6 (each 10 picomoles) each was dissolved in 30 μl of a buffer for T4 polynucleotide kinase reaction (50 mM Tris-HCl (pH 7.5), 10 mM MgCl$_2$, 5 mM dithiothreitol (hereinafter, DTT), 1 mM ATP, 0.1 mM spermidine, 0.1 mM EDTA). Following addition of 3 units of T4 polynucleotide kinase (Takara Shuzo), the phosphorylation reaction was carried out at 37° C. for 40 minutes. Thereafter, the enzyme was inactivated by heating at 65° C. for 15 minutes. A 4-μl portion was taken from each reaction mixture thus obtained. The 4-μl portions from the four reaction mixtures were combined, 0.08 picomole of DNA 7 (obtained in the above manner) was added. The volume of the mixture was increased to 50 μl, with addition of 2 units of T4 DNA ligase (Takara Shuzo), while the mixture composition was adjusted to: 28 mM Tris-HCl (pH 7.5), 9 mM MgCl$_2$, 10 mM DTT, 0.03 mM EDTA, 0.7 mM ATP and 0.03 mM spermidine. The ligation reaction was effected at 4° C. for 16 hours.

The reaction mixture was used to transform the *Escherichia coli* HB101 strain (Bolivar et al., *Gene*, 2, 75 (1977)) by the method of Cohen et al (S. N. Cohen et al., *Proc. Natl. Acad. Sci. USA*, 69 2110 (1972)), and ampicillin-resistant (Ap$^r$) colonies were obtained. The plasmid DNA was recovered from one of the colonies by the alkali treatment method (Maniatis et a. (ed.), *Molecular Cloning*, p. 368, Cold String Harbor Laboratory). Thus was obtained pMTA1. The structure of pMTA1 was confirmed by cleavage with BglII, PstI, SacI and BamHI, followed by agarose gel electrophoresis.

For each cleavage reaction in the presence of the enzyme concerned, a reaction medium was prepared by adding NaCl or KCl in an optimal concentration for said enzyme as selected within the range of 0–200 mM to a solution containing 10 mM Tris-HCl (pH 7.5)., 7 mM MgCl$_2$ and 6 mM 2-mercaptoethanol hereinafter, restriction enzyme reaction medium; the NaCl or KCl concentration alone being given hereinafter).

Furthermore, the desired [Leu$^{13}$]motilin gene was identified by determining the 115-base sequence covering the portions derived from DNAs 3–6 by the method described in the literature (A. J. H. Smith, *Methods in Enzymology*, edited by L. Grossmen and K. Moldave, vol. 65, p. 560 (1980), Academic Press).

EXAMPLE 3

Construction of the plasmid pMTA2:

A 0.2-μg portion of the plasmid pMTA1 obtained in Example 2 was dissolved in 15 μl of the restriction enzyme reaction medium (100 mM NaCl) defined in Example 2, 6 units of PstI (Takara Shuzo) and 6 units of BglII (Toyo Jozo) were added, and the digestion reaction was effected at 37° C. for 2 hours. The reaction mixture was fractionated by the same agarose gel electrophoresis as carried out in Example 2. Thus was obtained a DNA fragment (DNA 8) of about 2.8 kb.

Separately, 0.2 μg of pMTA1 was dissolved in 15 μl of the restriction enzyme reaction medium (100 mM KCl), 6 units of PstI and 6 units of BamHI (Takara Shuzo) were added, and the digestion reaction was effected at 37° C. for 2 hours. Fractionation of the reaction mixture by agarose gel electrophoresis gave a DNA fragment (DNA 9) about 1.2 kb in length.

The thus-obtained DNA 8 (50 ng) and DNA 9 (50 ng) were combined and dissolved in 30 μl of a medium for T4 DNA ligase reaction (20 mM Tris-HCl (pH 7.5), 10 mM MgCl$_2$, 10 mM DTT, 0.3 mM ATP), 1 unit of T4 DNA ligase (Takara Shuzo) was added, the the ligation reaction was effected at 4° C. for 18 hours. The reaction mixture was used to transform the *Escherichia coli* HB101 strain, and Ap$^r$ colonies were isolated. The plasmid DNA was recovered from one of said colonies. Thus was obtained pMTA2. The structure of this plasmid was confirmed by cleavage with PstI, BamHI and BglII, followed by agarose gel electrophoresis.

EXAMPLE 4

Construction of the plasmid pMTA4:

A 0.2-μg portion of the plasmid pMTA2 obtained in Example 3 was dissolved in 15 μl of the restriction enzyme reaction medium (100 mM NaCl) defined in Example 2, 6 units of PstI and 6 units of BglII were added, and the plasmid was digested at 37° C. for 2 hours. Fractionation by agarose gel electrophoresis gave a DNA fragment about 2.8 kb in length. Separately, 0.2 μg of pMTA2 was dissolved in 15 μl of the restriction enzyme reaction medium (100 mM KCl), 6 units of PstI and 6 units of BamHI were added and digestion was effected at 37° C. for 2 hours. Fractionation by agarose gel electrophoresis gave a DNA fragment about 1.3 kb in length.

The above two DNA fragment (each 8.2 picomole) were combined and dissolved in 30 μl of the T4 DNA ligase reaction medium, i unit of T4 DNA ligase was added, and the ligation reaction was effected at 4° C. for 18 hours. The reaction mixture was used to transform the *Escherichia coli*

HB101 strain, Ap$^r$ colonies were isolated, the the plasmid DNA was recovered. The structure of the thus-obtained plasmid pMTA4 was confirmed by the cleavage with PstI, BamHI and BglII, followed by agarose gel electrophoresis.

EXAMPLE 5

Construction of the plasmid pMTL4:

A 1-μg portion of the plasmid psGHIM1 was dissolved in 30 μl of the restriction enzyme reaction medium (100 mM KCl), 6 units of PstI and 6 units of BamHI were added, and the digestion reaction was effected at 37° C. for 2 hours. A DNA fragment of about 2.1 kb was recovered by agarose gel electrophoresis.

The plasmid pGHD7 (1 μg) was digested with PstI and BamHI in the same manner as in the case of psGHIM1, and a DNA fragment of about 1.7 kb was recovered.

These DNA fragment (each 0.03 picomole) were combined and dissolved in 30 μl of the T4 DNA ligase reaction medium, 1 unit of T4 DNA ligase was added, and the ligation reaction was effected at 4° C. for 18 hours. The reaction mixture was used to transform the *Escherichia coli* HB101 strain, Ap$^r$ colonies were isolated, and the plasmid DNA was recovered. Thus was obtained psGHIME1.

A 0.5-μg portion of the thus-obtained plasmid psGHIME1 was dissolved in 30 μl of the restriction enzyme reaction medium (neither NaCl nor KCl added), 50 units of SacI (Takara Shuzo) was added, and the digestion reaction was effected at 37° C. for 2 hours. Then, 2 μl of 2M NaCl was added and further 15 units of BglII was added, and the digestion reaction was continued at 37° C. for additional 2 hours. A DNA fragment of about 3.2 kb was recovered following fractionation by agarose gel electrophoresis.

A 0.5-μg portion of pMTA4 (obtained in Example 4) was digested in the same manner as above with SacI and then with BglII, and a DNA fragment of about 0.3 kb was recovered by agarose gel electrophoresis.

These DNA fragments (each 0.03 picomole) were combined and dissolved in 30 μl of the T4 DNA ligase reaction medium, 1 unit of T4 DNA ligase was added, and the ligation reaction was effected at 4° C. for 15 hours. The reaction mixture was used to transform the *Escherichia coli* HB101 strain, Ap$^r$ colonies were isolated, and the plasmid DNA was recovered. Thus was obtained pMTL4.

EXAMPLE 6

Construction of the plasmid pMTN4:

A 1.5-μg portion of the plasmid pMTL4 obtained in Example 5 was dissolved in 20 μl of the restriction enzyme reaction medium (100 mM NaCl), 8 units of PstI and 7 units of BglII were added, and the digestion reaction was effected at 37° C. for 2 hours. A DNA fragment of about 2.2 kb (DNA 15) was recovered by agarose gel electrophoresis. Separately, pMTL4 was dissolved in 20 μl of the restriction enzyme reaction medium (100 mM NaCl), 8 units of PstI and 6 units of HindIII (Takara Shuzo) were added, and the digestion reaction was effected at 37° C. for 2 hours. Following agarose gel electrophoresis, a DNA fragment of about 1.0 kb (DNA 16) was recovered.

DNA 15 (21 picomoles) and DNA 16 (21 picomoles) were each dissolved in 50 μl of the T4 polynucleotide kinase reaction buffer defined in Example 2, 4 units of T4 polynucleotide kinase was added, and the phosphorylation reaction was effected at 37° C. for 40 minutes. The enzyme was then inactivated by heating at 65° C. for 15 minutes. The reaction mixtures of (2 μl each) were combined, DNA 15 and DNA 16 were added, and the mixture was made 40 μl while adjusting the composition as follows, with addition of 2 units of T4 DNA ligase: 28 mM Tris-HCl, 9 mM MgCl$_2$, 10 mM DTT, 0.03 mM EDTA, 0.7 mM ATP, 0.03 mM spermidine. The ligation reaction was then effected at 4° C. for 16 hours. The reaction mixture was used to transform the *Escherichia coli* HB101 strain, Ap$^r$ colonies were isolated, and the plasmid DNA was recovered. Thus was obtained pMTN4.

EXAMPLE 7

Construction of the plasmid pMTO4:

A 2.5-μg portion of the plasmid pMTN4 was dissolved in 40 μl of the restriction enzyme reaction medium (neither NaCl nor KCl added) containing 0.01% of TRITON nonionic surfactant 12 units of SacI was added, and the digestion reaction effected at 37° C. for 2 hours. The reaction mixture was extracted with phenol-chloroform, and SacI-cleaved pMTN4 was recovered by precipitation with ethanol and dissolved in 40 μl of a solution having the composition: 20 mM Tris-HCl (pH 7.8), 7 mM MgCl$_2$, 6 mM 2-mercaptoethanol, 0.25 mM each dNTP (dATP, dTTP, dCTP, dGTP). To the solution was added 4 units of *Escherichia coli* DNA polymerase I, Klenow fragment (Takara Shuzo), and the reaction was effected at 20° C. for 1 hour. The reaction mixture was extracted with phenol-chloroform, and polymerase-treated pMTN4 fragment was recovered by precipitation with ethanol. This was dissolved in 30 μl of the restriction enzyme reaction medium (100 mM NaCl), 5 units of PstI was added, and the digestion reaction was effected for 2 hours. Fractionation by agarose gel electrophoresis gave a DNA fragment of about 1.3 kb (DNA 20).

A 2-μg portion of the plasmid pArgE1 was dissolved in 20 μl of the restriction enzyme reaction medium (150 mM NaCl), 10 units of PstI and 10 units of EcoRV (Takara Shuzo) were added, and the digestion reaction was effected at 37° C. for 2 hours. Fractionation by agarose gel electrophoresis gave a DNA fragment Of about 1.7 kb (DNA 19).

This DNA 19 (0.06 picomole) and DNA 20 (0.06 picomole) were combined and dissolved in 25 μl of the T4 DNA ligase reaction medium, 3 units of T4 DNA ligase was added, and the ligation reaction was effected at 4° C. for 20 hours. The reaction mixture was used to transform the *Escherichia coli* HB101 strain, Ap$^r$ colonies were isolated, and the plasmid DNA was recovered from one of the colonies. Thus was obtained pMTO4. The structure of pMTO4 was confirmed by cleavage with PstI, EcoRI, HindIII, SalI, BglII and MluI.

EXAMPLE 8

Construction of the plasmid pMTOI4:

The plasmid pMTO4 (2 μg) was dissolved in 30 μl of the restriction enzyme reaction medium (100 mM NaCl), 6 units of HindIII and 6 units of PstI were added, and the digestion reaction was effected at 37° C. for 2 hours. A [Leu$^{13}$]motilin polymer gene-containing DNA fragment of about 3.0 kb (DNA 21) was recovered by fractionation by agarose gel electrophoresis. Separately, 3 μg of the plasmid pKYP10 (European Patent Publication No. 83069A) was dissolved in 30 μl of the restriction enzyme reaction medium (100 mM NaCl), 9 units of HindIII and 9 units of PstI were added, the digestion reaction was effected at 37° C. for 2 hours, and a promoter-containing DNA fragment of about 1.1 kb (DNA 22) was recovered by fractionation by agarose gel electrophoresis. These DNA fragments (about 0.1 mg each) were dissolved in 30 μl of the T4 DNA ligase reaction medium, 1 unit of T4 DNA ligase was added, and the ligation reaction was effected at 4° C. for 18 hours. The reaction mixture was used to transform the *Escherichia coli* HB101 strain, and the plasmid DNA was recovered from one of the Ap$^r$ colonies obtained. Thus was obtained the [Leu$^{13}$]motilin polymer expression plasmid pMTOI4 containing a tryptophan promoter. The structure of pMTOI4 was confirmed by cleavage with PstI, BanIII, HindIII and MluI (cf. FIG. 9).

EXAMPLE 9

Construction of the plasmid pMTOII4:

The plasmid pMTO4 (2 µg) was dissolved in 30 µl of the restriction enzyme reaction medium (100 mM NaCl), 6 units of HindIII and 6 units of PstI were added, and the digestion reaction was effected at 37° C. for 2 hours. A [Leu$^{13}$]motilin polymer gene-containing DNA fragment of about 3.0 kb (DNA 21) was recovered by fractionation by agarose gel electrophoresis. Separately, 3 µg of the plasmid pGEL1 (European Patent Publication No. 166444A) was dissolved in 30 µl of the restriction enzyme reaction medium (100 mM NaCl), 9 units of HindIII and 9 units of PstI were added, and the digestion reaction was effected at 37° C. for 2 hours. A promoter-containing DNA fragment of about 1.1 kb (DNA 23) was recovered by fractionation by agarose gel electrophoresis. These DNA fragments (about 0.1 µg each) were dissolved in 30 µl of the T4 DNA ligase reaction medium, 1 unit of T4 DNA ligase was added, and the ligation reaction was effected at 4° C. for 18 hours. The reaction mixture was used to transform the *Escherichia coli* HB101 strain, and the plasmid DNA was recovered from one of the Ap$^r$ colonies obtained. Thus was obtained the plasmid pMTOII4 for [Leu$^{13}$]motilin polymer expression. The plasmid contained two tryptophan promoters coupled in series and, in the plasmid, the SD sequence was 14 bases apart from the initiation codon ATG. The structure of pMTOII4 was confirmed by cleavage with PstI, BanIII, HindIII and MluI (cf. FIG. 10).

EXAMPLE 10

Construction of the plasmid pMTOIII4:

The plasmid pMTO4 (2 µg) was dissolved in 30 µl of the restriction enzyme reaction medium (100 mM NaCl), 6 units of HindIII and 6 units of PstI were added, and the digestion reaction was effected at 37° C. for 2 hours. Following fractionation by agarose gel electrophoresis, a [Leu$^{13}$] motilin polymer gene-containing DNA fragment of about 3.0 kb was recovered. Separately, 3 µg of the plasmid pGHA2 (European Patent Publication No. 152613A) was dissolved in 30 µl of the restriction enzyme reaction medium (100 mM NaCl), 9 units of HindIII and 9 units of PstI were added, and the digestion reaction was effected at 37° C. for 2 hours. Following fractionation by agarose gel electrophoresis, a promoter-containing DNA fragment of about 0.9 kb was recovered. These DNA fragments (about 0.1 µg each) were dissolved in 30 µg of the T4 DNA ligase reaction medium, 1 unit of T4 DNA ligase was added, and the ligation reaction was effected at 4° C. for 18 hours. The reaction mixture was used to transform the *Escherichia coli* HB101 strain, the the plasmid DNA was recovered from one of the Ap$^r$ colonies obtained. Thus was obtained the plasmid pMTOIII4 for [Leu$^{13}$]motilin polymer expression, which contained a let promoter. The structure of pMTOIII4 was confirmed by cleavage with PstI, BanIII, HindIII, MluI and BglII (cf. FIG. 11).

EXAMPLE 11

Production of a [Leu$^{13}$]motilin polymer protein in *Escherichia coli* using the plasmid pMTO4:

The *Escherichia coli* W3110 strA strain (FERM BP-732) was transformed with pMTO4 (obtained in Example 7). An Ap$^r$ colony thus obtained was inoculated into 8 ml of LG medium (1% Bacto-tryptone, 0.5% yeast extract, 0.5% NaCl, 0.1% glucose, 50 µg/ml tryptophan, 50 µg/ml ampicillin, pH 7.5) and cultured at 30° C. for 16 hours. A 400-µl portion of the culture was inoculated into 10 ml of MEG medium (0.6% Na$_2$HPO$_4$, 0.3% KH2PO$_4$, 0.5% NaCl, 0.1% NH$_4$Cl, 0.5% glucose, 0.5% casamino acids, 1 mM MgSO$_4$, 4 µg/ml vitamin B1, pH 7.2) supplemented with 50 µg/ml tryptophan and 50 µg/ml ampicillin and cultured at 30° C. When the turbidity (OD$_{550}$) of the culture had reached 0.9 (after about 4 hours), 200 µg of indoleacrylic acid was added. The cultivation was continued for a further 4 hours. Then, cells were recovered by centrifuging the culture at 7,000 rpm for 5 minutes. The cells were dissolved in the sample buffer of Laemmli et al. (*Nature*, 227, 680 (1970)), and the solution was heated and subjected to SDS-polyacrylamide gel electrophoresis after the method of Laemmli et al. As a result of staining with Coomassie Brilliant Blue, a polypeptide band was detected at a position corresponding to a molecular weight of about 15,000. the *Escherichia coli* W3110 strA strain free from pMTO4 gave no corresponding band. It was thus established that the pMTO4-carrying transformant of *Escherichia coli* W3110 strA had produced a [Leu$^{13}$]motilin polymer protein as fused with a part of the salmon growth hormone.

EXAMPLE 12

Production of a Leu$^{13}$ motilin polymer protein in *Escherichia coli* using the plasmid pMTOI4:

The *Escherichia coli* W3110 strA strain transformed with the plasmid pMTOI4 obtained in Example 8. An Ap$^r$ colony obtained was cultured in the same manner as in Example 11, and cells were recovered by centrifuging the culture at 7,000 rpm for 5 minutes. The cells were dissolved in the sample buffer according to Laemmli et al., and the solution was heated and subjected to SDS-polyacrylamide gel elecrtrophoresis after the method of Laemmli et al., followed by Coomassie Brilliant Blue staining. As a result, a polypeptide band was detected at a position corresponding to a molecular weight of about 15,000. Since the pMTOI4-free *Escherichia coli* W3110 strA strain gave no corresponding band, it was evident that the pMTOI4-carrying transformant of *Escherichia coli* W3110 strA had produced a [Leu$^{13}$]motilin polymer protein as fused with a part of the salmon growth hormone.

EXAMPLE 13

Production of a [Leu$^{13}$]motilin polymer protein in *Escherichia coli* using the plasmid pMTOII4:

The plasmid pMTOII4 obtained in Example 9 was used to transform the *Escherichia coli* W3110 strA strain. An Ap$^r$ colony obtained was cultured in the same manner as in Example 11, and cells were recovered by centrifuging the culture at 7,000 rpm for 5 minutes. The cells were dissolved in the sample buffer of Laemmli et al., and the solution was heated and subjected to SDS-polyacrylamide gel electrophoresis after the method of Laemmli et al., followed by Coomassie Brilliant Blue staining. As a result, a polypeptide band was detected at a position corresponding to a molecular weight of about 15,000. Since the pMTOII4-free *Escherichia coli* W3110 strA strain gave no corresponding band, it was evident that the pMTOII4-carrying transformant of *Escherichia coli* w3110 strA had produced a [Leu$^{13}$]motilin polymer protein as fused with a part of the salmon growth hormone.

EXAMPLE 14

Production of a Leu$^{13}$ motilin polymer protein in *Escherichia coli* using the plasmid pMTOIII4:

The plasmid pMTOIII4 obtained in Example 10 was used to transform the *Escherichia coli* W3110 strA strain. An Ap$^r$ colony obtained was cultured in the same manner as in Example 11, and cells were recovered by centrifuging the culture at 7,000 rpm for 5 minutes. The cells were dissolved in the sample beffer of Laemmli et al., and the solution was heated and subjected to SDS-polyacrylamide gel electrophoresis after the method of Laemmli et al., followed by Coomassie Brilliant Blue staining. As a result, a polypeptide band was detected at a position corresponding to a molecular weight of about 15,000. Since the pMTOIII4-free *Escherichia coli* W3110 strA strain gave no corresponding band, it was evident that the pMTOIII4-carrying transformant of *Escherichia coli* W3110 strA had produced a [Leu$^{13}$]motilin polymer protein as fused with a part of the salmon growth hormone.

EXAMPLE 15

Production of a Leu$^{13}$ motilin polymer protein in *Escherichia coli* using plasmid pMTN4:

The plasmid pMTN4 obtained in Example 6 was used to transform the *Escherichia coli* W3110 strA strain. An Ap$^r$ colony obtained was cultured into 8 ml of LG medium, followed by cultivation at 30° C. for 8 hours. A part of the culture was inoculated into 10 ml of LG medium. After 16 hours of cultivation at 30° C., the culture was inoculated into 1 liter of MCG medium supplemented with 100 µg/ml tryptophan and 50 µg/ml ampicillin, and cultivation was carried out in a jar fermenter at 30° C. for 48 hours.

A 100-ml portion of the culture was centrifuged at 7,000 rpm. The cells thus recovered were washed with PSG (97 mM disodium phosphate, 1.5 mM potassium dihydrogen phosphate, 137 mM NaCl, 2.7 mM KCl), suspended in 60 ml of PBS and sonicated for 30 minutes. The sediment obtained by centrifugation at 10,000 rpm for 40 minutes was dissolved in 3.48 ml of 20 mM sodium phosphate buffer (pH 7.0), followed by addition of 3 ml of distilled water, 3.6 ml of 1.5M NaCl and 25 ml of Percol (Pharmacia Fine Chemicals) and centrifugation at 17,000 rpm for 15 minutes. The sediment was fractionated into two fractions according to the Percol density gradient, and a higher-density fraction was recovered. To this fraction was added 5 volumes of distilled water. Centrifugation at 11,000 rpm for 7 minutes gave a sediment, which was washed with distilled water to give 47 mg of granules. The protein guantitation was performed by using a protein assay kit (Bio-Rad).

EXAMPLE 16

Production of [Leu$^{13}$]motilin monomer:

The granular motilin polymer obtained in Example 15 (about 5 mg) was dissolved in 2.0 ml of 70% formic acid, a solution of 42 mg of cyanogen bromide in 0.4 ml of 70% formic acid was added, and the mixture was allowed to stand at 37° C. for 1 day. Again, 0.4 ml of a solution of 42 mg of cyanogen bromide in 70% formic acid was added, and the whole mixture was allowed to stand overnight at 37° C. The product composed of [Leu$^{13}$]motilin monomer and the spacer peptide residue bound thereto (peptide 25) was isolated by high performance liquid chromatography (HPLC). An about 100-µg portion of the peptide isolated was dissolved in 0.4 ml of 0.2M N-ethylmorpholine acetate buffer (pH 8.0), and the solution was allowed to stand at 37° C. for 21 hours, whereby the homoserine-derived lactone ring at the carboxyl terminus of peptide 25 was cleaved. Then, 2 µg of carboxypeptidase A (Sigma) was added, and the mixture was allowed to stand at 37° C. for 30 minutes to give peptide 26 composed of [Leu$^{13}$]motilin and arginine bound to the carboxyl terminus of the [Leu$^{13}$]motilin. An about 22-µg portion of this peptide 26 was dissolved in 0.2 ml of 0.2M N-ethylmorpholine acetate buffer (pH 8.0), 1 µg of carboxypeptidase B (Sigma) was added, and the mixture was allowed to stand at 37° C. for 10 minutes. Thereafter, 0.2 ml of 0.1% trifluoroacetic acid solution was added to thereby terminate the reaction. In this way, [Leu$^{13}$]motilin was obtained in a quantitative yield. The structure of this [Leu$^{13}$]motilin was confirmed by amino acid sequence analysis and mass analysis.

EXAMPLE 17

Intestine-contracting activity of [Leu$^{13}$]motilin:

Male rabbits weighing 2.3–2.8 kg were sacrificed by exsanguination, and duodenum specimens, about 1.5 cm long, were excised. Each duodenum specimen was suspended in a 30-ml Magnus bath, the lower end was tied to an isotonic transducer (Nihon Kohden model TD-112S), and the contractile respond to the duodenum was recorded on a recorder (Yokogawa Hokushin Electric type 3066). The duodenum was loaded with a tension of 1 g.

The experiment was carried out at a temperature of 28°±1° C. in a mixed gas atmosphere composed of 95% $O_2$ and 5% $CO_2$, using as the nutritive solution Tyrode solution (8.0 g/l NaCl, 0.2 g/l KCl, 0.2 g/l $CaCl_2$, 0.1 g/l $MgCl_2$, 0.05 g/l $NaH_2PO_4$, 1.0 g/l $NaHCO_3$, 1.0 g/l glucose).

Figure 17:
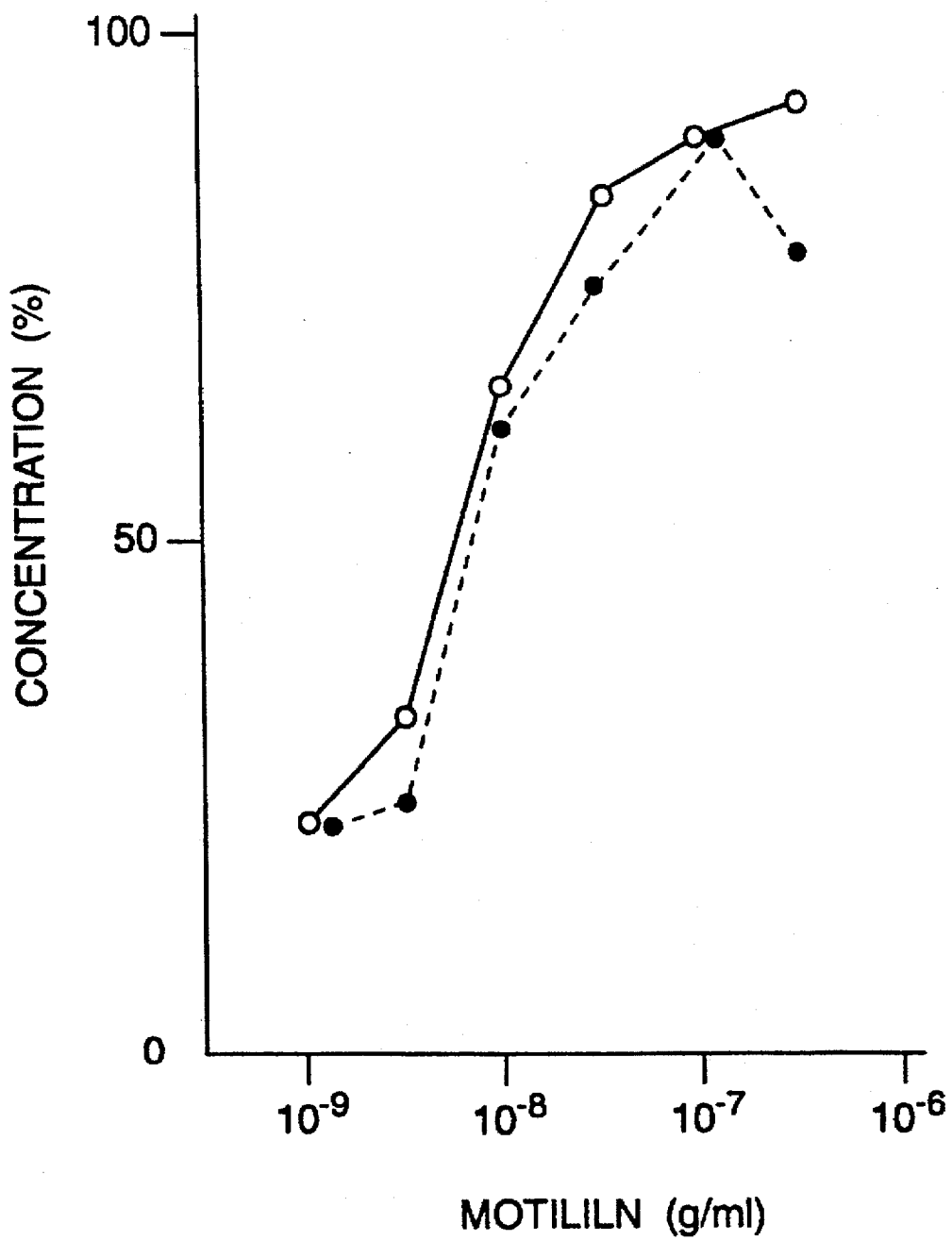
FIG. 17 shows the intestine-contracting activity of [Met$^{13}$]motilin and that of [Leu$^{13}$]motilin, wherein ○ is for [Leu$^{13}$]motilin and ● for [Met$^{13}$]motilin.

For evaluating the contracting activity of [Met$^{13}$]motilin and that of [Leu$^{13}$]motilin, the contractile tensions obtained upon cumulative addition thereof to Tyrode solution to concentrations of $1 \times 10^{-9}$ to $3 \times 10^{-7}$ g/ml were measured and the measured values were compared with the contractile tension measured following addition of $10^{-5}$ g/ml of acetylcholine and expressed in percentages with the value for acetylcholine being taken as 100%. The results obtained, which are shown in FIG. 17, show that [Leu$^{13}$]motilin is comparable in intestine-contracting activity to naturally occurring porcine motilin.

REFERENCE EXAMPLE 1

Figure 12:
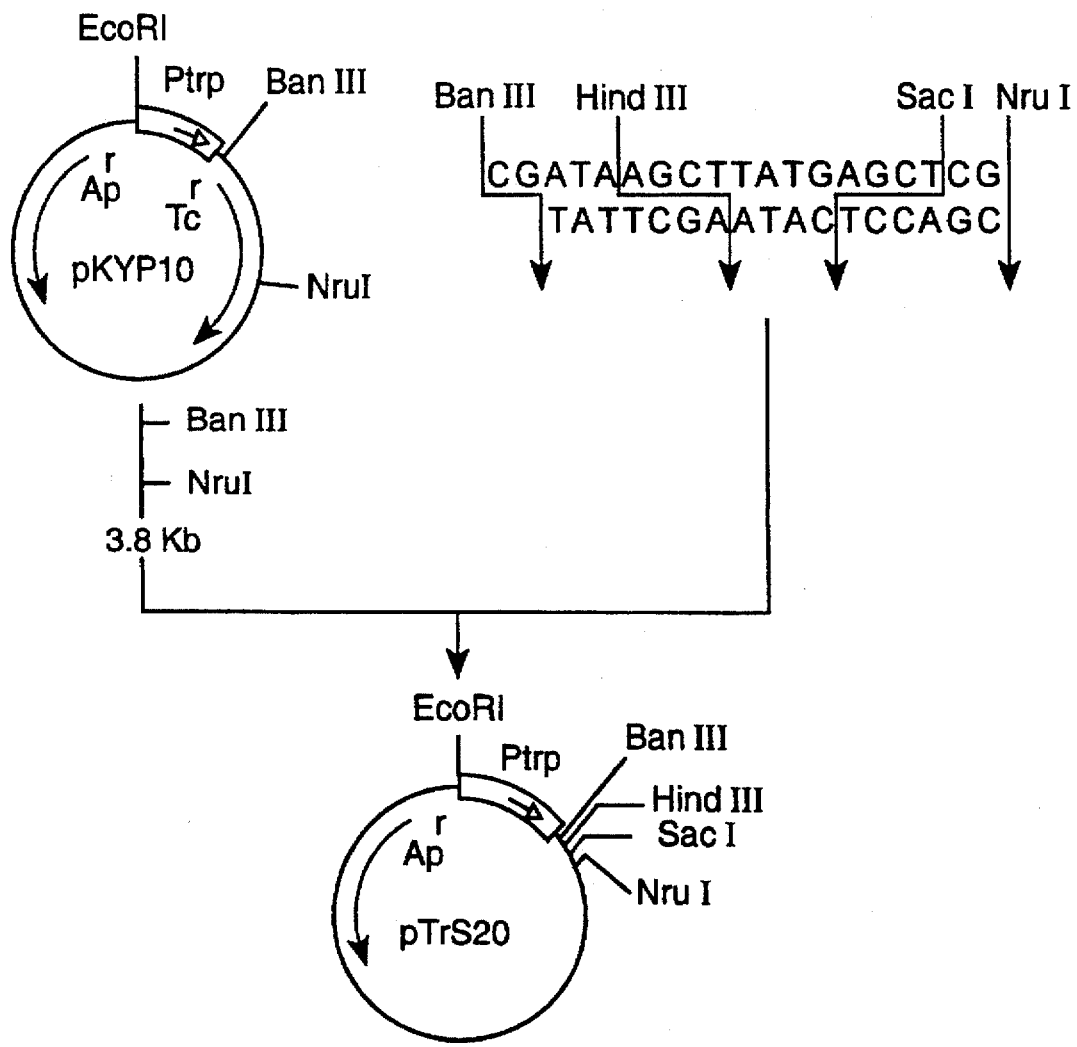
FIG. 12 shows a construction scheme for the plasmid pTrS20.

Construction of the ATG vector pTrS20:

Following the scheme shown in FIG. 12, the ATG vector pTrS20 was constructed. In this vector, the SD sequence is 14 bases apart from the initiation codon ATG, and the vector contains a SacI site immediately behind the ATG codon.

First, 3 µg of pKYP10 prepared by the method described in European Patent Publication No. 83069A was dissolved in 30 µl of Y-100 buffer, 6 units each of the restriction enzymes BanIII and NruI (New England BioLabs) were added, and the cleavage reaction was effected at 37° C. for 3 hours. From the reaction mixture, there was obtained, by the LGT method, about 0.5 µg of a Ptrp-containing DNA fragment of about 3.8 kb (BanIII-NruI fragment).

Separately, for providing the initiation codon ATG downstream from Ptrp, the following DNA linker was synthesized by the phosphotriester method:

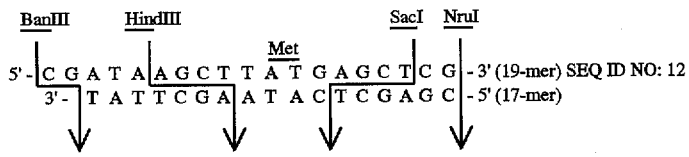

The 19-mer and 17-met synthetic DNAs (10 picomoles each) were dissolved in a total volume of 20 μl of a solution containing 50 mM Tris-HCl (pH 7.5), 10 mM MgCl$_2$, 5 mM dithiothreitol, 0.1 mM EDTA and 1 mM ATP, followed by addition of 3 units of T4 polynucleotide kinase (Takara Shuzo). The phosphorylation reaction was then carried out at 37° C. for 60 minutes.

Then, 0.1 μg of the above-mentioned pKYP10-derived BanIII-NruI fragment (about 3.8 kb) and about 0.5 picomole of the above-mentioned DNA linker were dissolved in 20 μl of T4 ligase buffer and, in addition, 2 units of T4 DNA ligase was added. Then, the ligation reaction was conducted at 4° C. for 18 hours.

The thus-obtained recombinant plasmid mixture was used to transform the *Escherichia coli* HB101 strain (Boliver et al., *Gene*, 2, 75 (1977)), and Ap$^r$ colonies were isolated. The plasmid DNA was recovered from the cultured cells derived from one of the colonies. The structure of the plasmid obtained was confirmed by agarose gel electrophoresis following cleavage with the restriction enzymes EcoRI, BanIII, HindIII, SacI and NruI. This plasmid was named pTrS20. pTrS20 has the base sequence shown below in the neighborhood of the BanIII and HindIII sites was confirmed by the dideoxy sequencing method using M13 phage.

The reaction mixture was used to transform the *Escherichia coli* HB101 strain (Boliver et al., *Gene*, 2, 75 (1977)) by the method of Cohen et al. (S. N. Cohen et al., *Proc. Natl. Acad. Sci.* USA, 69, 2110 (1972)), and Ap$^r$ colonies were isolated. The plasmid DNA was separated from one of the transformant strains by the known method (H. C. Birnboim et al., *Nucleic Acids Res.*, 7, 1513 (1979)). Thus was obtained pGEL10 (about 3.4 kb). The structure of pGEL10 was confirmed by agarose gel electrophoresis following cleavage with EcoRI, PstI, HindIII and BamHI. The base sequence from the SD sequence downstream from the trp promoter to the translation initiation codon ATG for the interferon-γ gene was determined by the Maxam-Gilbert method (*Proc. Natl. Acad. Sci.*, USA, 74, 560 (1977)) and found to include 10 bp as follows:

A A G G G T A T A A G C T T A T G  SEQ ID NO: 15
SD                            Met

The plasmid pGEL10 (5 μg) obtained above was dissolved in 40 μl of Y-100 buffer, 10 units each of HindIII and BamHI were added, and the cleavage reaction was effected at 37° C. for 3 hours. From the reaction mixture, there was recovered about 2 μg of a DNA fragment (about 2.7 kb)

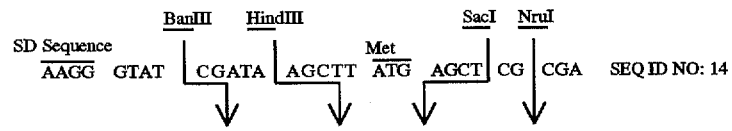

REFERENCE EXAMPLE 2

Figure 15:
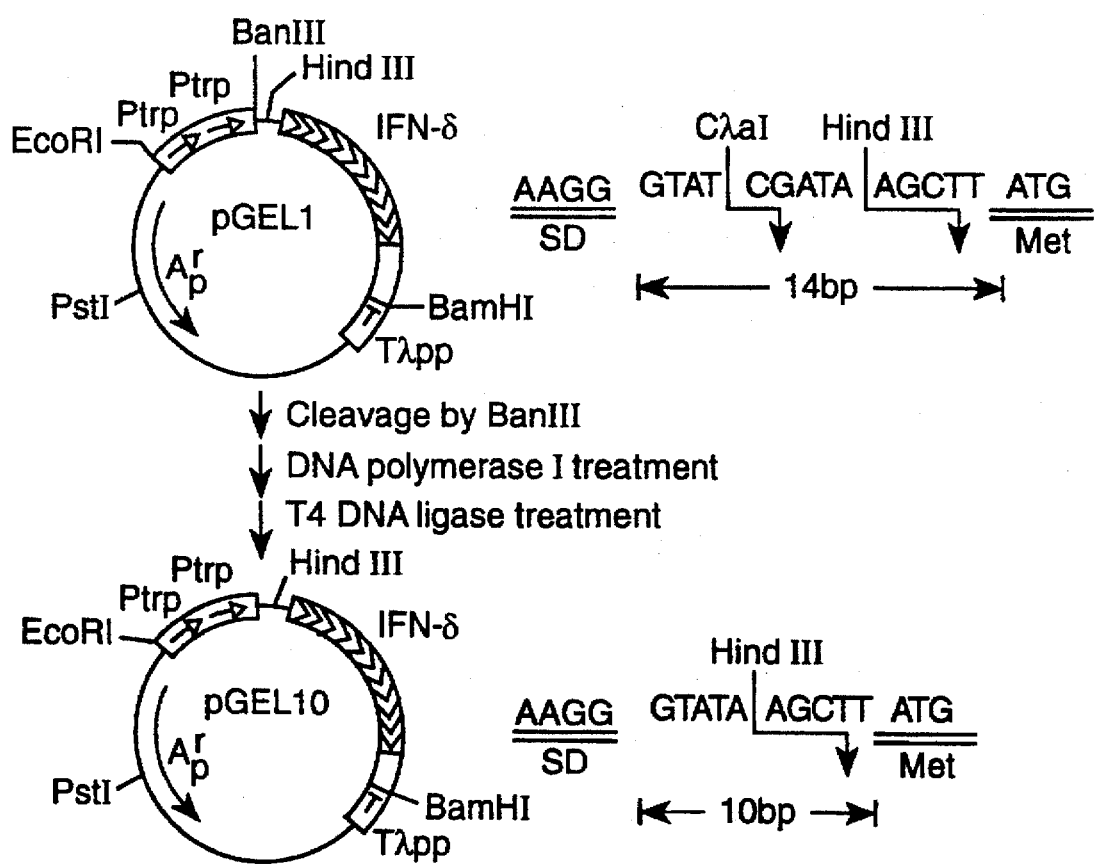
FIG. 15 shows a construction scheme for the plasmid pGEL10.
Figure 16:
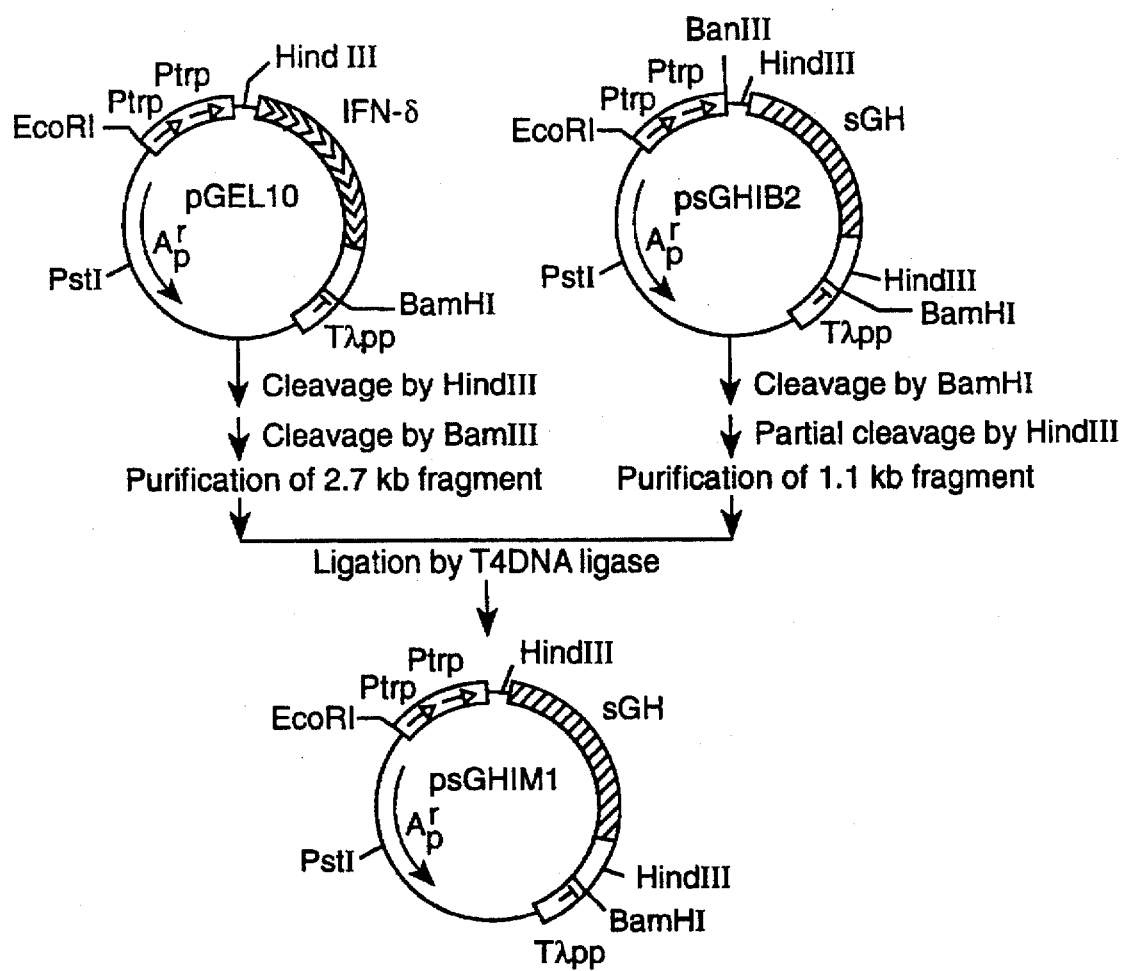
FIG. 16 shows a construction scheme for the plasmid psGHIM1.

Construction of the salmon growth hormone expression plasmid psGHIM1 (FIGS. 15 and 16):

In 40 μl of a solution (hereinafter, "Y-100 buffer") containing 20 mM Tris-HCl (pH 7.5), 10 mM MgCl$_2$ and 100 mM NaCl, there was dissolved 3 μg of pGEL1 (about 3.4 kb), followed by addition of 5 units of BanIII (Toyobo). Then the digestion reaction was effected at 37° C. for 3 hours. Extraction of the reaction mixture with phenol and precipitation with ethanol gave about 2.4 mg of pGEL1, the product of cleavage at one BanIII site. This DNA fragment (about 2.4 mg) was dissolved in 50 μl of a solution (hereinafter, "DNA polymerase buffer") containing 50 mM Tris-HCl (pH 7.8), 7 mM MgCl$_2$ and 6 mM mercaptoethanol, dATP and dTTP were added each to a concentration of 1 mM, 5 units of DNA polymerase I (New England Bio-Labs) was further added, and the reaction was effected at 37° C. for 30 minutes to thereby scrape off the projecting ends. About 2.0 μg of a DNA fragment was recovered by extraction with phenol and precipitation with ethanol. A 1-μg portion of said DNA fragment was dissolved in 30 μl of a buffer (hereinafter, "T4 ligase buffer I") containing 20 mM Tris-HCl (pH 7.6), 10 mM MgCl$_2$, 10 mM dithiothreitol and 1 mM ATP, 2 units of T4 DNA ligase (Takara Shuzo: hereinafter the same shall apply) was added, and the ligation reaction was conducted at 4° C. for 8 hours.

containing the trp promoter region, origin of replication and lipoprotein terminator by the freezing-thawing method.

Separately, about 5 μg of psGHIB2 (about 3.8 kb) (prepared by the method of Reference Example 3) was dissolved in 40 μl of Y-100 buffer, 10 units of BamHI were added, and the reaction was carried out at 37° C. for 3 hours to complete cleavage. Then, i unit of HindIII was added, and the reaction was carried out at 37° C. for 30 minutes for partial cleavage. From the reaction mixture, there was recovered about 0.7 μg of a DNA fragment (about 1.1 kb) coding for the mature-form salmon growth hormone by the freezing-thawing method.

About 0.1 μg of the DNA fragment of pGEL10 and about 0.2 μg of the DNA fragment of psGHIB2, both as recovered in the above manner, were dissolved in 30 μl of T4 DNA ligase buffer I, 2 units of T4 DNA ligase was added, and the ligation reaction was effected at 4° C. for 18 hours. The reaction mixture was used to transform the *Escherichia coli* HB101 strain, and the plasmid DNA was recovered from one of the colonies obtained. Thus was obtained psGHIM1. The structure of psGHIM1 was confirmed by agarose gel electrophoresis following cleavage with EcoRI, HindIII, BamHI and PstI.

REFERENCE EXAMPLE 3

Construction of the recombinant plasmid psGHIB2 coding for the mature-form salmon growth hormone:

A 5-μg of the plasmid psGH1 (prepared by the method described in European Patent Publication No. 166444A) containing a DNA coding for the salmon growth hormone was dissolved in 40 μl of a solution (hereinafter, "Y-10 buffer") containing 20 mM Tris-HCl (pH 7.5), 10 mM MgCl$_2$, and 10 mM NaCl, 10 units of the restriction enzyme MboII (New England BioLabs) was added, and the digestion reaction was effected at 37° C. for 3 hours. Then, the NaCl concentration in the resulting solution was adjusted to 175 mM, 10 units of SalI was added, and the digestion reaction was performed at 37° C. for 3 hours. From the reaction mixture, there was obtained, by the LGT method, about 0.2 μg of a 163 bp DNA fragment corresponding to the N terminus and its neighborhood.

Then, 5 μg of psGH1 was dissolved in 40 μl of Y-100 buffer, 10 units of BamHI was added, and the digestion reaction was effected at 37° C. for 3 hours. The NaCl concentration of the reaction mixture was then adjusted to 175 mM, 10 units of SalI was added, and the digestion reaction was carried out at 37° C. for 3 hours. From the reaction mixture, there was obtained, by the LTG method, about 0.5 μg of a DNA fragment (about 900 bp) containing the C-terminal side and the 3'-nontranslational region.

Separately, 5 μg of pGEL1 was dissolved in 40 μl of Y-100 buffer, 10 units each of BamHI and HindIII were added, and the digestion reaction was carried out at 30° C. for 3 hours. From the reaction mixture, there was obtained about 1 μg of a tryptophan promoter-containing DNA fragment (about 2.7 kb).

Further, separately, a DNA linker having the sequence given below was synthesized for introducing the translation initiation codon required for the expression of the DNA coding for the mature-form salmon growth hormone and for linking the vector DNA and the above DNA.

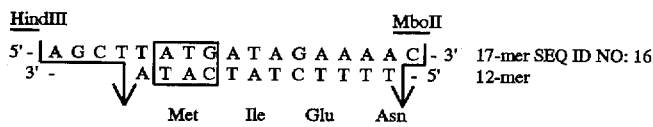

First, the single-stranded 17-mer and 12-mer DNAs were synthesized by the conventional phosphotriester method (R. Crea et al., *Proc. Natl. Acad. Sci.*, USA, 75, 5765 (1978)). The 17-mer and 12-mer single-stranded DNAs (12 picomoles each) were dissolved in 20 μl of a solution containing 50 mM Tris-HCl (pH 7.5), 10 mM MgCl$_2$, 10 mM dithiothreitol and 1 mM ATP, 6 units of T4 polynucleotide kinase (Takara Shuzo) were added, and the phosphorylation reaction was carried out at 37° C. for 60 minutes.

The psGH1-derived MboII-SalI fragment (163 bp) (0.1 picomole), 0.06 picomole of the SalI-BamHI fragment (about 900 bp) and 0.02 picomole of the pGEL1-derived HindIII-BamHI fragment (about 2.7 kb), each obtained as described above, were dissolved in 30 μl of a solution containing 50 mM Tris-HCl (pH 7.5), 10 mM MgCl$_2$, 10 mM dithiothreitol and 1 mM ATP. To the solution was added 5 μl of the phosphorylated synthetic DNA-containing reaction mixture mentioned above. To the resultant mixture was added 6 units of T4 ligase (Takara Shuzo), and the ligation reaction was effected at 4° C. for 18 hours.

The reaction mixture was used to transform the *Escherichia coli* HB101 strain, Ap$^r$ colonies were isolated, and the plasmid DNA was recovered from one of the colonies. Thus was obtained psGHIB2 shown in FIG. 16. The structure of psGHIB2 was confirmed by agarose gel electrophoresis following cleavage with EcoRI, HindIII, ClaI, BglII, SalI and BamHI. The sequence in the neighborhood of the N terminus of the DNA coding for the salmon growth hormone in psGHIB2 was determined by the Sanger's method using M13 phage and found to be as follows:

As a result, it was found that psGHIB2 contains a DNA coding for the mature-form salmon growth hormone polypeptide. A strain of *Escherichia coli* carrying the plasmid psGHIB2, namely *Escherichia coli* ESGHIB2, has been deposited as of Sep. 20, 1984 at the Fermentation Research Institute, Agency of Industrial Science and Technology under the deposit number FERM BP-612.

REFERENCE EXAMPLE 4

Figure 13:
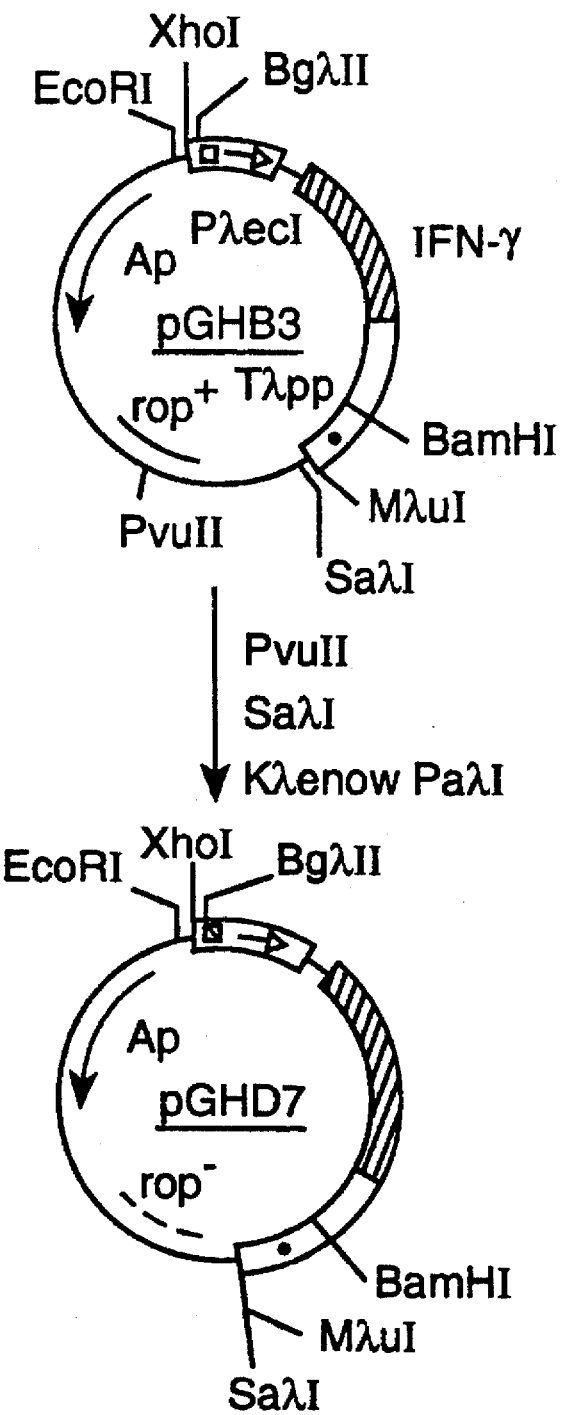
FIG. 13 shows a construction scheme for the plasmid pGHD7.

Construction of the plasmid pGHD7 (FIG. 13):

About 2 μg of the plasmid pGHB3 (European Patent Publication No. 152613A; IGHB3, FERM BP-403) carrying the lecI promoter (of European Patent Publication No. 152613A), *Escherichia coli* lipoprotein gene (1 pp) terminator and human interferon-γ cDNA was dissolved in 30 μl of Y-50 buffer (buffer containing 10 mM Tris-HCl (pH 7.5), 50 mM NaCl, 7 mM MgCl$_2$ and 6 mM 2-mercaptoethanol), 8 units of PvuII were added, and the digestion reaction was conducted at 37° C. for 2 hours.

Then, NaCl was added to make its concentration 150 mM, 8 units of SalI were added, and the digestion reaction was further conducted at 37° C. for 2 hours. The DNA fragment obtained by extraction of the mixture resulting from the digestion reaction with phenol and chloroform and precipitation with ethanol was dissolved in a total volume of 30 μl of a buffer containing 50 mM Tris-HCl (pH 7.6), 7 mM MgCl$_2$, 6 mM 2-mercaptoethanol, 0.25 mM dATP, 0.25 mM dCTP, 0.25 mM dGTP and 0.24 mM dTTP, 4 units of *Escherichia coli*-derived DNA polymerase I, Klenow fragment (Takara Shuzo) was added, and the reaction was carried out at 15° C. for 2 hours to thereby convert the projecting ends resulting from digestion to blunt ends. After 10 minutes of heat treatment at 65° C., the larger DNA fragment (3.6 kb) was purified by low-melting-point agarose gel electrophoresis.

The thus-obtained DNA fragment (about 0.1 μg) was subjected to ligation. The ligation reaction was performed in 20 μl of a buffer containing 20 mM Tris-HCl (pH.7.6), 10 mM MgCl$_2$, 10 mM dithiothreitol and 8.5 mM ATP (hereinafter, "T4 DNA ligase buffer II") in the presence of 2 units of T4 DNA ligase at 4° C. for 18 hours.

The thus-obtained recombinant plasmid DNA was used to transform the *Escherichia coli* HB101 strain, and ampicillin-resistant strains were isolated. The plasmid DNA was isolated from one of the transformant strains and analyzed for its structure. As a results, it was confirmed that the plasmid pGHD7 having the desired structure had been constructed.

REFERENCE EXAMPLE 5

Figure 14:
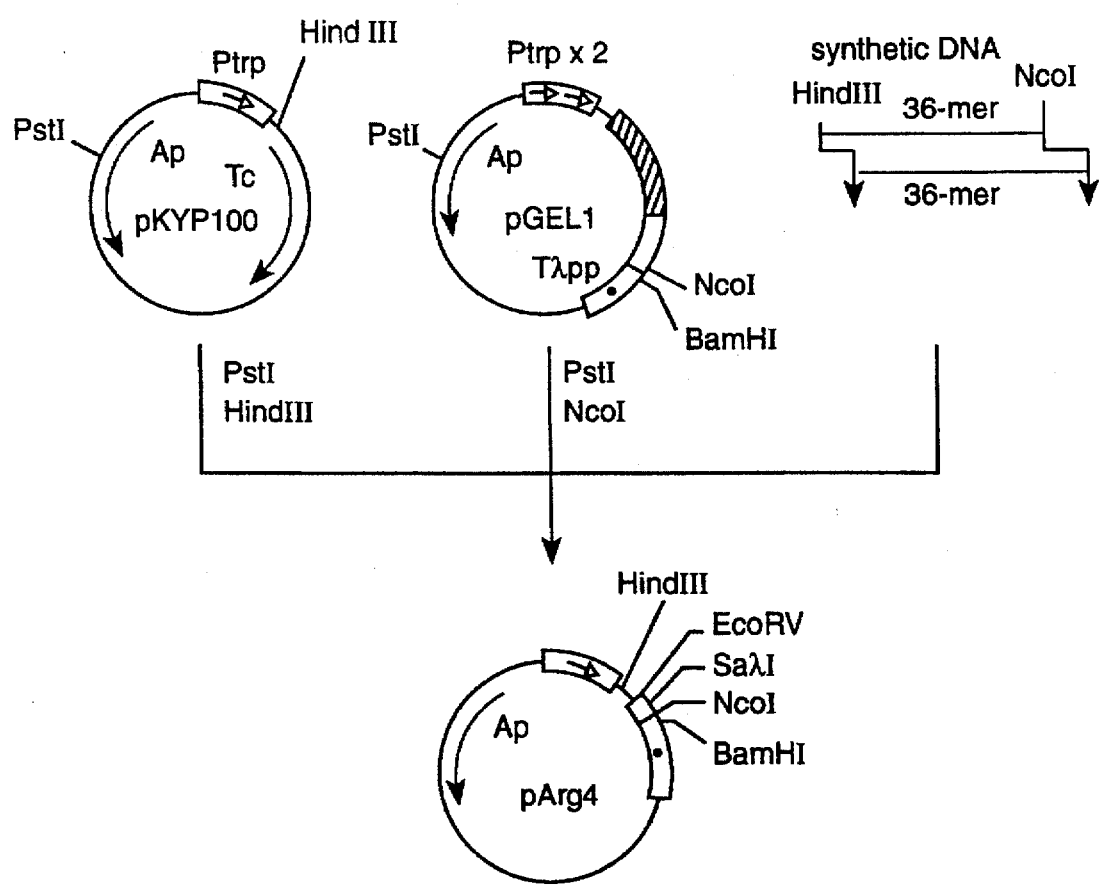
FIG. 14 shows a construction scheme for the plasmid pArg4.

Construction of the plasmid pArg4 (FIG. 14):

About 3 μg of the trp portable promoter-containing plasmid pKYP100 (T. Nishi et al., *Agric. Biol. Chem*, 48, 669–675 (1984)) was dissolved in 30 μl of a buffer containing 10 mM Tris-HCl (pH 7.5), 50 mM NaCl, 7 mM MgCl$_2$ and 6 mM 2-mercaptoethanol, 10 units of PstI and 10 units of HindIII were added, and the digestion reaction was effected at 37° C. for 2 hours. After 10 minutes of heat treatment at 65° C., the smaller DNA fragment (0.88 kb) was purified by low-melting-point agarose gel electrophoresis.

Furthermore, about 3 μg of the human interferon-γ expression plasmid pGEL1 (FERM BP-612; European Patent Publication No. 166444A) was dissolved in 30 μl of Y-100 buffer, 10 units of PstI and 10 units of NcoI were added, and the digestion reaction was conducted at 37° C. for 2 hours. After 10 minutes of heat treatment at 65° C., the larger DNA fragment (1.7 kb) was purified by low-melting-point agarose gel electrophoresis.

A DNA linker (having the EcoRV site and SalI site within itself) was designed for use in coupling the two purified DNA fragments mentioned above, as follows: SEQ ID NO:19

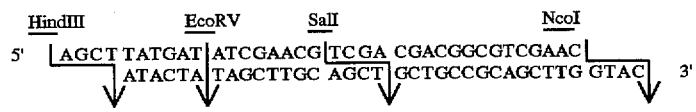

Thus, two single-stranded DNAs (each 36-mer) shown above were synthesized by the conventional phosphotriester method (R. Crea et al., *Proc. Natl. Acad. Sci.*, USA, 75, 5765 (1978)). Each DNA (20 picomoles) was dissolved in a total volume of 20 μl of a solution containing 50 mM Tris-HCl (pH 7.5), 10 mM MgCl$_2$, 5 mM dithiothreitol, 0.1 mM EDTA and 1 mM ATP, 4 units of T4 polynucleotide kinase was added, and the phosphorylation reaction was conducted at 37° C. for 30 minutes. Equal amounts of these single-stranded DNAs were mixed, heated at 65° C. for 5 minutes and then gradually cooled to room temperature, whereby a DNA linker having the above structure was obtained.

This DNA linker (1 picomole) and the two above-mentioned purified DNA fragments (0.1 μg each) were ligated together in 20 μl of of the above-mentioned T4 ligase buffer II in the presence of 2 units of T4 DNA ligase at 4° C. The ligation reaction was performed for 18 hours.

The thus-obtained recombinant plasmid DNA was used to transform the *Escherichia coli* HB101 strain, and ampicillin-resistant strains were obtained. The plasmid DNA was isolated from one of these transformant strains and analyzed for its structure. It was confirmed that there had been constructed he plasmid pArg4 having the desired structure.

While the invention has been described in detail and with reference to specific embodiments thereof, it will be apparent to one skilled in the art that various changes and modifications can be made therein without departing from the spirit and scope thereof.

---

What is claimed is:

1. A method of producing a peptide having the amino acid sequence set forth in SEQ ID NO:1 which method comprises the steps of:

(a) cultivating, in a nutrient growth medium, a microorganism harboring an expression vector which contains a recombinant DNA coding for a peptide having said amino acid sequence inserted therein and allowing the peptide having said amino acid sequence to be expressed and to accumulate in the cultivated cells, and (b) harvesting said peptide from said cells.

2. A method of producing a peptide having the amino acid sequence set forth in SEQ ID NO:1 which comprises degrading a peptide having the amino acid sequence set forth in SEQ ID NO:10 with carboxypeptidase A and carboxypeptidase B.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide -continued ( i x ) FEATURE:
    ( A ) NAME/KEY: Peptide
    ( B ) LOCATION: 1..22
    ( D ) OTHER INFORMATION: /product="[LEU13]MOTILIN"

( x i ) SEQUENCE DESCRIPTION: SEQ ID NO:1:

```
Phe Val Pro Ile Phe Thr Tyr Gly Glu Leu Gln Arg Leu Gln Glu Lys
 1           5                   10                  15
Glu Arg Asn Lys Gly Gln
            20
```

( 2 ) INFORMATION FOR SEQ ID NO:2:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:2:

CGATCAGATC TTCATGTTCG TTCCGATTTT CACTTACGGT GAACTGCAAC     50

( 2 ) INFORMATION FOR SEQ ID NO:3:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:3:

AGTTCACCGT AAGTGAAAAT CGGAACGAAC ATGAAGATCT GAT     43

( 2 ) INFORMATION FOR SEQ ID NO:4:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:4:

GTCTGCAAGA GAAAGAACGT AACAAAGGTC AGCGGATCCT GTAAGAGCT     49

( 2 ) INFORMATION FOR SEQ ID NO:5:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:5:

CTTACAGGAT CCGCTGACCT TGTTACGTT CTTTCTCTTG CAGACGTTGC     50

( 2 ) INFORMATION FOR SEQ ID NO:6:

( i ) SEQUENCE CHARACTERISTICS:
( A ) LENGTH: 99 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:6:

```
CGATCAGATC TTCATGTTCG TTCCGATTTT CACTTACGGT GAACTGCAAC GTCTGCAAGA    60
GAAAGAACGT AACAAGGTC AGCGGATCCT GTAAGAGCT                            99
```

( 2 ) INFORMATION FOR SEQ ID NO:7:

( i ) SEQUENCE CHARACTERISTICS:
( A ) LENGTH: 93 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:7:

```
CTTACAGGAT CCGCTGACCT TTGTTACGTT CTTTCTCTTG CAGACGTTGC AGTTCACCGT    60
AAGTGAAAAT CGGAACGAAC ATGAAGATCT GAT                                 93
```

( 2 ) INFORMATION FOR SEQ ID NO:8:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:8:

```
AGCTTATGAT AGAAAACCAA CGGCTCTTCC A                                   31
```

( 2 ) INFORMATION FOR SEQ ID NO:9:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:9:

```
GATCTGGAAG AGCCGTTGGT TTTCTATCAT A                                   31
```

( 2 ) INFORMATION FOR SEQ ID NO:10:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 26
( D ) OTHER INFORMATION: /note= "Xaa is homoserine."

( x i ) SEQUENCE DESCRIPTION: SEQ ID NO:10:

Phe Val Pro Ile Phe Thr Tyr Gly Glu Leu Gln Arg Leu Gln Glu Lys
1               5                   10                  15
Glu Arg Asn Lys Gly Gln Arg Ile Phe Xaa
            20              25

( 2 ) INFORMATION FOR SEQ ID NO:11:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:11:

Phe Val Pro Ile Phe Thr Tyr Gly Glu Leu Gln Arg Leu Gln Glu Lys
1               5                   10                  15
Glu Arg Asn Lys Gly Gln Arg
            20

( 2 ) INFORMATION FOR SEQ ID NO:12:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "SYNTHETIC DNA"

( x i ) SEQUENCE DESCRIPTION: SEQ ID NO:12:

CGATAAGCTT ATGAGCTCG                                                                                          19

( 2 ) INFORMATION FOR SEQ ID NO:13:

( i ) SEQUENCE CHARACTERISTICS:
      ( A ) LENGTH: 17 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "SYNTHETIC DNA"

( x i ) SEQUENCE DESCRIPTION: SEQ ID NO:13:

CGAGCTCATA AGCTTAT                                                                                            17

( 2 ) INFORMATION FOR SEQ ID NO:14:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: misc_feature
      ( B ) LOCATION: 1..4
      ( D ) OTHER INFORMATION: /note= "Shine-Dalgano sequence"

( x i ) SEQUENCE DESCRIPTION: SEQ ID NO:14:

AAGGGTATCG ATAAGCTTAT GAGCTCGCGA                                                                              30

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AAGGGTATAA GCTTATG                                        17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:16:

AGCTTATGAT AGAAAAC                                        17

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:17:

TTTTCTATCA TA                                                12

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:18:

AAGCTTATGA TAGAAAACCA A                                21

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:19:

AGCTTATGAT ATCGAACGTC GACGACGGCG TCGAAC            36

( 2 ) INFORMATION FOR SEQ ID NO:20:

(  i  ) SEQUENCE CHARACTERISTICS:
    ( A ) LENGTH: 36 base pairs
    ( B ) TYPE: nucleic acid
    ( C ) STRANDEDNESS: double
    ( D ) TOPOLOGY: linear (  i i  ) MOLECULE TYPE: other nucleic acid
    ( A ) DESCRIPTION: /desc = "SYNTHETIC DNA"

(  x i  ) SEQUENCE DESCRIPTION: SEQ ID NO:20:

CATGGTTCGA CGCCGTCGTC GACGTTCGAT ATCATA    36

( 2 ) INFORMATION FOR SEQ ID NO:21:

(  i  ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear (  i i  ) MOLECULE TYPE: peptide (  v  ) FRAGMENT TYPE: internal (  x i  ) SEQUENCE DESCRIPTION: SEQ ID NO:21:

Arg Ile Phe Met
1